US011686734B2

(12) United States Patent
Subramanyam et al.

(10) Patent No.: US 11,686,734 B2
(45) Date of Patent: *Jun. 27, 2023

(54) METHODS AND PRODUCTS FOR EVALUATING AN IMMUNE RESPONSE TO A THERAPEUTIC PROTEIN

(71) Applicant: Biogen MA Inc., Cambridge, MA (US)

(72) Inventors: Meena Subramanyam, Stoneham, MA (US); Lakshimi Amaravadi, Natick, MA (US); Eric Wakshull, Princeton, MA (US); Frances Lynn, Somerville, MA (US); Michael Panzara, Winchester, MA (US); Robin McDaid Barbour, Walnut Creek, CA (US); Julie Elizabeth Taylor, San Francisco, CA (US)

(73) Assignee: BIOGEN MA INC., Cambridge, MA (US)

( * ) Notice: Subject to any disclaimer, the term of this patent is extended or adjusted under 35 U.S.C. 154(b) by 318 days.

This patent is subject to a terminal disclaimer.

(21) Appl. No.: 16/923,043

(22) Filed: Jul. 7, 2020

(65) Prior Publication Data

US 2021/0025900 A1 Jan. 28, 2021

Related U.S. Application Data

(63) Continuation of application No. 15/616,669, filed on Jun. 7, 2017, now Pat. No. 10,705,095, which is a continuation of application No. 14/330,619, filed on Jul. 14, 2014, now Pat. No. 9,709,575, which is a continuation of application No. 13/242,505, filed on Sep. 23, 2011, now Pat. No. 8,871,449, which is a continuation of application No. 11/887,782, filed as application No. PCT/US2006/012493 on Apr. 4, 2006, now Pat. No. 8,124,350.

(60) Provisional application No. 60/668,404, filed on Apr. 4, 2005.

(51) Int. Cl.
  *G01N 33/68* (2006.01)
  *C07K 16/28* (2006.01)

(52) U.S. Cl.
  CPC ..... *G01N 33/6854* (2013.01); *C07K 16/2839* (2013.01); *G01N 33/686* (2013.01); *G01N 2333/70546* (2013.01); *G01N 2800/065* (2013.01); *G01N 2800/102* (2013.01); *G01N 2800/285* (2013.01); *G01N 2800/52* (2013.01)

(58) Field of Classification Search
  None
  See application file for complete search history.

(56) References Cited

U.S. PATENT DOCUMENTS

| | | |
|---|---|---|
| 3,639,350 A | 2/1972 | Lazaraus et al. |
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,235,601 A | 11/1980 | Deutsch et al. |
| 4,275,149 A | 6/1981 | Litman et al. |
| 4,277,437 A | 7/1981 | Maggio |
| 4,366,241 A | 12/1982 | Tom et al. |
| 4,376,110 A | 3/1983 | David et al. |
| 4,391,904 A | 7/1983 | Litman et al. |
| 4,399,216 A | 8/1983 | Axel et al. |
| 4,425,112 A | 1/1984 | Ito |
| 4,472,509 A | 9/1984 | Gansow et al. |
| 4,517,288 A | 5/1985 | Giegel et al. |
| 4,634,665 A | 1/1987 | Axel et al. |
| 4,703,017 A | 10/1987 | Campbell et al. |
| 4,818,677 A | 4/1989 | Hay-Kaufman et al. |
| 4,837,168 A | 6/1989 | de Jaeger et al. |
| 4,938,948 A | 7/1990 | Ring et al. |
| 4,943,522 A | 7/1990 | Eisinger et al. |
| 5,096,837 A | 3/1992 | Fan et al. |
| 5,118,428 A | 6/1992 | Sand et al. |
| 5,118,630 A | 6/1992 | Glaze |
| 5,179,017 A | 1/1993 | Axel et al. |
| 5,221,616 A | 6/1993 | Kolb et al. |
| 5,223,220 A | 6/1993 | Fan et al. |
| 5,225,328 A | 7/1993 | Chang |
| 5,329,459 A | 7/1994 | Kaufman et al. |
| 5,415,994 A | 5/1995 | Imrich et al. |
| 5,434,057 A | 7/1995 | Dorian |
| 5,521,102 A | 5/1996 | Boehringer et al. |
| 5,530,101 A | 6/1996 | Queen et al. |

(Continued)

FOREIGN PATENT DOCUMENTS

| | | |
|---|---|---|
| EP | 0239400 A2 | 9/1987 |
| EP | 1712913 A1 | 10/2006 |

(Continued)

OTHER PUBLICATIONS

Lloyd et al., Protein Engineering, Design & Selection 22:159-168 (Year: 2009).*
Edwards et al., J Mol Biol. Nov. 14, 2003;334(1): 103-118 (Year: 2003).*
U.S. Appl. No. 17/700,242, entitled, "Anti-VLA-4 Related Assays", filed Mar. 21, 2022, of Biogen MA Inc. (Published as US 2022-0357338 A1 on Nov. 10, 2022).

(Continued)

*Primary Examiner* — Phuong Huynh
(74) *Attorney, Agent, or Firm* — Todd Lorenz

(57) ABSTRACT

The invention relates to methods and products for the identification of a clinically significant immune response in subjects treated with a therapeutic protein. Aspects of the invention relate to methods and compositions for identifying a clinically significant immune response in patients treated with therapeutic amounts of a VLA4 binding antibody (e.g., natalizumab).

11 Claims, 5 Drawing Sheets

(56) References Cited

U.S. PATENT DOCUMENTS

| | | |
|---|---|---|
| 5,536,646 A | 7/1996 | Sand et al. |
| 5,541,069 A | 7/1996 | Mortensen et al. |
| 5,559,041 A | 9/1996 | Kang et al. |
| 5,585,089 A | 12/1996 | Queen et al. |
| 5,648,260 A | 6/1997 | Winter et al. |
| 5,686,315 A | 11/1997 | Pronovost et al. |
| 5,693,761 A | 12/1997 | Queen et al. |
| 5,693,762 A | 12/1997 | Queen et al. |
| 5,712,172 A | 1/1998 | Huang et al. |
| 5,763,262 A | 6/1998 | Wong et al. |
| 5,766,961 A | 6/1998 | Pawlak et al. |
| 5,770,460 A | 6/1998 | Pawlak et al. |
| 5,773,234 A | 6/1998 | Pronovost et al. |
| 5,786,220 A | 7/1998 | Pronovost et al. |
| 5,789,650 A | 8/1998 | Lonberg et al. |
| 5,798,230 A | 8/1998 | Bornkamm et al. |
| 5,804,452 A | 9/1998 | Pronovost et al. |
| 5,814,455 A | 9/1998 | Pronovost et al. |
| 5,840,299 A | 11/1998 | Bendig et al. |
| 5,845,255 A | 12/1998 | Mayaud |
| 5,849,992 A | 12/1998 | Meade et al. |
| 5,888,507 A | 3/1999 | Burkly |
| 5,939,331 A | 8/1999 | Burd et al. |
| 6,014,631 A | 1/2000 | Teagarden et al. |
| 6,187,598 B1 | 2/2001 | May et al. |
| 6,238,859 B1 | 5/2001 | Luke et al. |
| 6,305,377 B1 | 10/2001 | Portwood et al. |
| 6,306,642 B1 | 10/2001 | Nelson et al. |
| 6,352,862 B1 | 3/2002 | Davis et al. |
| 6,407,213 B1 | 6/2002 | Carter et al. |
| 6,485,982 B1 | 11/2002 | Charlton |
| 6,534,320 B2 | 3/2003 | Ching et al. |
| 6,602,503 B1 | 8/2003 | Lobb |
| 6,620,626 B1 | 9/2003 | Bodily |
| 6,623,981 B2 | 9/2003 | O'Neil et al. |
| 6,767,714 B2 | 7/2004 | Nazareth et al. |
| 6,790,611 B2 | 9/2004 | Lassen et al. |
| 7,291,477 B2 | 11/2007 | Alderete et al. |
| 7,419,666 B1 | 9/2008 | Iliaki et al. |
| 7,807,167 B2 | 10/2010 | Taylor et al. |
| 8,124,350 B2 * | 2/2012 | Subramanyam ..... G01N 33/686 435/7.1 |
| 8,871,447 B2 * | 10/2014 | Kayed ................ A61K 39/0007 435/7.1 |
| 8,871,449 B2 | 10/2014 | Subramanyam et al. |
| 9,316,641 B2 | 4/2016 | Gorelik et al. |
| 9,709,575 B2 * | 7/2017 | Subramanyam ... C07K 16/2839 |
| 10,705,095 B2 * | 7/2020 | Subramanyam ..... G01N 33/686 |
| 2001/0021910 A1 | 9/2001 | Goldstein |
| 2002/0001852 A1 | 1/2002 | Mendel-Hartvig et al. |
| 2002/0052543 A1 | 5/2002 | Williams et al. |
| 2003/0032923 A1 | 2/2003 | Eakins et al. |
| 2003/0070185 A1 | 4/2003 | Jakobovits et al. |
| 2003/0232333 A1 | 12/2003 | Ladner et al. |
| 2004/0009169 A1 | 1/2004 | Taylor et al. |
| 2004/0248216 A1 | 12/2004 | Seino |
| 2005/0130120 A1 | 6/2005 | Lambotte et al. |
| 2005/0215869 A1 | 9/2005 | Elsayed et al. |
| 2005/0244985 A1 | 11/2005 | Freitag et al. |
| 2005/0283385 A1 | 12/2005 | Hunkeler et al. |
| 2006/0246513 A1 | 11/2006 | Bohannon |
| 2007/0190667 A1 | 8/2007 | Cole et al. |
| 2007/0231319 A1 | 10/2007 | Yednock |
| 2008/0038759 A1 | 2/2008 | Keren et al. |
| 2008/0044382 A1 | 2/2008 | Lieberburg |
| 2008/0233150 A1 | 9/2008 | Smith et al. |
| 2009/0176256 A1 | 7/2009 | Subramanyam et al. |
| 2009/0216107 A1 | 8/2009 | Rubin et al. |
| 2009/0232702 A1 | 9/2009 | Wu et al. |
| 2010/0112725 A1 | 5/2010 | Babu et al. |

FOREIGN PATENT DOCUMENTS

| | | |
|---|---|---|
| EP | 1933140 A1 | 6/2008 |
| EP | 1872136 B1 | 2/2015 |
| EP | 2645106 B1 | 6/2017 |
| JP | 2003511697 A | 3/2003 |
| JP | 2005214670 A | 8/2005 |
| JP | 2007197441 A | 8/2007 |
| JP | 8507680 A | 3/2008 |
| JP | 2009-528359 A | 8/2009 |
| JP | 2009531304 A | 9/2009 |
| WO | WO 90/07861 A1 | 7/1990 |
| WO | WO 94/16094 A2 | 7/1994 |
| WO | WO 96/34096 A1 | 10/1996 |
| WO | WO 03/016909 A1 | 2/2003 |
| WO | WO 03/072040 A2 | 9/2003 |
| WO | WO 04/043237 A2 | 5/2004 |
| WO | WO 06/107962 A2 | 10/2006 |
| WO | WO 2007/103112 A2 | 9/2007 |

OTHER PUBLICATIONS

U.S. Appl. No. 16/422,822, entitled, "Anti-VLA-4 Related Assays", filed May 24, 2019, of Biogen MA Inc. (Issued as U.S. Pat. No. 11,280,793 on Mar. 22, 2022).

U.S. Appl. No. 15/637,446, entitled, "Anti-VLA-4 Related Assays", filed Jun. 29, 2017, of Biogen MA Inc. (Issued as U.S. Pat. No. 10,302,654 on May 28, 2019).

U.S. Appl. No. 15/166,514, entitled, "Anti-VLA-4 Related Assays", filed May 27, 2016, of Biogen MA Inc. (Issued as U.S. Pat. No. 9,726,672 on Aug. 8, 2019).

U.S. Appl. No. 13/501,111, entitled, "Anti-VLA-4 Related Assays", filed May 27, 2016, of Plavina et al. (Issued as U.S. Pat. No. 9,377,458 on Jun. 28, 2006).

U.S. Appl. No. 16/923,043, entitled, "Methods and Products for Evaluating an Immune Response to a Therapeutic Protein," filed Jul. 7, 2020, of Biogen MA Inc. (Published as US 2021-0025900 A1 on Jan. 28, 2021).

U.S. Appl. No. 15/616,669, entitled, "Methods and Products for Evaluating an Immune Response to a Therapeutic Protein," filed Jun. 7, 2017, of Biogen MA Inc. (Issued as U.S. Pat. No. 10,705,095 on Jul. 7, 2020).

U.S. Appl. No. 14/330,619, entitled, "Methods and Products for Evaluating an Immune Response to a Therapeutic Protein," filed Jul. 14, 2014, of Biogen MA Inc. (Issued as U.S. Pat. No. 9,709,575 on Jul. 18, 2017).

U.S. Appl. No. 13/242,505, entitled, "Methods and Products for Evaluating an Immune Response to a Therapeutic Protein," filed Sep. 23, 2011, of Subramanyam et ak, (Issued as U.S. Pat. No. 8,871,449 on Oct. 28, 2014).

U.S. Appl. No. 11/887,782, entitled, "Methods and Products for Evaluating an Immune Response to a Therapeutic Protein," filed Mar. 19, 2009, of Subramanyam et al. (Issued as U.S. Pat. No. 8,124,350 on Feb. 28, 2012).

[No Author Listed] Approval letter for natalizumab by the FDA dated Nov. 23, 2004.

[No Author Listed] the Medical Letter on Drugs and Therapeutics, vol. 47, Issue 1202, Published in New Rochelle, NY on Feb. 14, 2005 by The Medical Letter, Inc.

[No Author Listed] ClinicalTrials.gov C-1801 and C-1802 dated Nov. 7, 2015.

[No Author Listed] Letter dated Nov. 19, 2013 from Biogen representative to EPO.

[No Author Listed] Pharmacopeia, 2013, first supplement: "<1106> Immunogenicity Assays—Design and Validation of Immunoassays to detect Anti-Drug Antibodies", pp. 5732-5744.

[No Author Listed] Prescribing info of Tysabri (natalizumab), 2015 30 pages.

[No Author Listed] Tysabri° (Natalizumab) Immunogenecity Test from Viracor-IBT Laboratories(available at http://www.viracoribt.com/Resource_/TestDetailPdf/Tysabrir-Natalizumab-Immunogenicity-Test-30040.pdf) (accessed on Mar. 8, 2016).

Abbing et al., "Efficient Intracellular Delivery of a Protein and a Low Molecular Weight Substance via Recombinant Polyomavirus-like Particles", The Journal of Biological Chemistry, vol. 279, No. 25, pp. 27410-27421, (2004).

(56) References Cited

OTHER PUBLICATIONS

Agostini et al., "JC Virus (JCV) Genotypes in Brain Tissue from Patients with Progressive Multifocal Leukoencephalopathy (PML) and in Urine from Controls without PML: Increased Frequency of JCV Type 2 in PML", Journal of Infectious Diseases, vol. 176, No. 1, p. 6, (1997).
Attwood, Teresa K., "The Babel of bioinformatics." Science 290. 5491 (2000): 471-473.
Baker, David, and Andrej Sali. "Protein structure prediction and structural genomics." Science 294.5540 (2001): 93-96.
Baert, F. et al., Influence of immunogenicity on the long-term efficacy of infliximab in Crohn's disease. N Engl J Med. Feb. 13, 2003;348(7):601-8.
Behzad-Behbahani, A., et al. "Detection of BK virus and JC virus DNA in urine samples from immunocompromised (HIV-infected) and immunocompetent (HIV-non-infected) patients using polymerase chain reaction and microplate hybridisation." Journal of clinical virology 29.4 (2004): 224-229.
Berthelot-Ruff et al., Immunisation apres immunoscintigraphies par anticorps monoclonaux murins; analyse de 692 dossiers. Immunoanal Biol Spec. 1999;14:308-314.
Biogen Idec and Elan Announce Update on TYSABRIZ; https://web.archive.org/web/20050403035414/http://www.elan.com:80/.
Biogen press release "FDA grants accelerated approval of TYSABRI, formerly antegren, for the treatment of MS", Public Release: Nov. 23, 2004, downloaded from www.eurekalert.org.
Biorad Anti-Drug Antibody (ADA) Bridging ELISA protocol—ADA Natalizumab.
Bloomgren et al., "Risk of Natalizumab-Associated Progressive Multifocal Leukoencephalopathy", The New England Journal of Medicine, vol. 366, p. 1874, (2012).
Boerner et al., "Production of antigen-specific human monoclonal antibodies from in vitro-primed human splenocytes," J. Immunol., vol. 147, pp. 86-95 (1991).
Bozic et al., "Anti-John Cunningham virus antibody prevalence in multiple sclerosis patients: baseline results of STRATIFY-1." Ann Neurol. http://www.nbci.nlm.nih.gov/pubmed/22162056>2011 Nov; 70(5):742-50. doi: 10.1002/ana.22606.
Braun et al., Oligonucleotide and plasmid DNA packaging into polyoma VP1 virus-like particles expressed in *Escherichia coli* Biotechnol. Appl. Biochem. (1999) 29, 31-43.
Brown, "Natalizumab in the treatment of multiple sclerosis," Therapeutics and Clinical Risk Management (2009) vol. 5, pp. 585-594.
Burton, D.R. and Woof, J.M, "Human Antibody Effector Function," Adv. Immunol., vol. 51, pp. 1-84 (1992).
Calabresi et al., The incidence and clinical significance of antibodies to Natalizumab: 1-year results from the SENTINEL study. 15th Annual Meeting of the Neurological Society. Vienna, Austria. Jun. 18-22, 2005. Meeting Poster. P493.
Calabresi, P.A. et al., Safety and tolerability of natalizumab: results from the SENTINEL trial. Neurology. Mar 2005;A277.
Calabresi et al., "The incidence and significance of anti-natalizumab antibodies: results from AFFIRM and SENTINEL", Neurology, vol. 69,Nr:14,pp. 1391-1403.
Casal J I, "Use of the baculovirus expression system for the generation of virus-like particles.", Biotechnology & Genetic Engineering Reviews 2001, vol. 18, 2001, pp. 73-87.
Chang et al., "Self-assembly of the JC virus major capsid protein, VP1, expressed in insect cells", Journal of General Virology (1997), vol. 78, pp. 1435-1439.
Cheung, N.K. et al., Anti-G(D2) antibody treatment of minimal residual stage 4 neuroblastoma diagnosed at more than 1 year of age. J Clin Oncol. Sep. 1998;16(9):3053-60.
Delos, Sue E., et al. "Expression of the polyomavirus minor capsid proteins VP2 and VP3 in *Escherichia coli*: in vitro interactions with recombinant VP1 capsomeres." Journal of virology 69.12 (1995): 7734-7742.
Egli et al., "Prevalence of polyomavirus BK and JC infection and replication in 400 healthy blood donors", J. Infect Dis. 199:837-846, 2009.

Enns et al., Enact-2 safety, tolerability, and immunogenicity results of natalizumab in patients with Crohn's disease. Am J Gastroenterol. Oct. 2004; 99 Suppl 5269.
EP Search Report for EP 07 81 3941 dated Mar. 21, 2013.
European Public Assessment Report of the EMA (EPAR) for Tysabri.
Extended European Search Report for EP 10 82 2820 dated Apr. 4, 2013.
Extended European Search Report for European Application No. 14803732 dated Nov. 15, 2016.
Experimental report of PRA Healthscience.
Focus Diagnostics safety data sheet for 12C4.
Giovannoni et al., Optimising MS disease-modifying therapies: antibodies in perspective. J Neurol. Sep. 2004;251 Suppl 5:v30-v35.
Giovannoni et al., Sa.32. The immunogenicity of natalizumab in patients with multiple sclerosis. Clin. Imm. 2006;119:S116.
Goelz Ph.D , "Assay design and sample collection can affect anti-John Cunningham virus antibody detection" Annals of Neurology, vol. 69, Issue 2, <http://onlinelibrary.wiley.com/doi/10.1002/ana.v69.2/issuetoc>pp. 429-430, Feb. 2011.
Goldmann et al., "Molecular cloning and expression of major structural protein VP1 of the human polyomavirus JC virus: formation of virus-like particles useful for immunological and therapeutic studies" Journal of Virology, vol. 73, No. 5, pp. 4465-4469, 1999.
Gorelik et al., "Anti-JC Virus Antibodies: Implications for PML Risk Stratification", Ann Neurol, vol. 68, No. 3, p. 295-303, (2010).
Green et al., "Antigen—specific human monoclonal antibodies from mice engineered with human Ig heavy and light chain YACs," Nature Genetics, vol. 7, pp. 13-21 (1994).
Hemler, M.E. et al., Characterization of the cell surface heterodimer VLA-4 and related peptides. J Biol Chem. Aug. 25, 1987;262(24):11478-85.
Hoesel, W. et al., Development and evaluation of a new ELISA for the detection and quantification of antierythropoietin antibodies in human sera. J Immunol Methods. Nov. 2004;294(1-2):101-10. Epub Oct. 4, 2004.
Hoogenboom et al., "Antibody phage display technology and its applications," Immunotechnology, vol. 4, pp. 1-20 (1998).
"Hoogenboom et al., "'Natural and designer binding sites made by phage display technology,"' Immunol Today, vol. 21, No. 8, pp. 371-378 (2000)".
Huang; Stollar, "Construction of representative immunoglobulin variable region cDNA libraries from human peripheral blood lymphocytes without in vitro stimulation," J. Immunol. Methods, vol. 141, pp. 227-236 (1991).
Hwang et al., Immunogenicity of engineered antibodies. Methods. May 2005;36(1):3-10.
International Preliminary Report on Patentability for PCT/US2007/075577 dated Feb. 10, 2009.
International Preliminary Report on Patentability for PCT/US2011/020832 dated Jul. 17, 2012.
International Search Report and Written Opinion for Application No. PCTUS1439525 dated Oct. 20, 2014.
International Search Report and Written Opinion for PCT/US12/40283 dated Dec. 17, 2012.
International Search Report for PCT/US10/52172 dated Dec. 14, 2010.
International search report for PCT/US2007/075577 dated Oct. 30, 2008.
International Search Report for PCT/US2011/020832 dated Mar. 14, 2011.
Issekutz, T.B. and Wykretowicz, A. Effect of a new monoclonal antibody, TA-2, that inhibits lymphocyte adherence to cytokine stimulated endothelium in the rat. J Immunol. Jul. 1, 1991;147(1):109-16.
Jefferis et al., "IgG-Fc-mediated effector functions: molecular definition of interaction sites for effector ligands and the role of glycosylation," Immunol. Rev., vol. 163, pp. 59-76 (1998).
Jilek et al., "Immune responses to JC virus in patients with multiple sclerosis treated with natalizumab: a cross-sectional and longitudinal study", Lancet Neurology (published online Jan. 29, 2010), vol. 9, Mar. 2010, pp. 264-272.

(56) References Cited

OTHER PUBLICATIONS

Kappos et al., The incidence and clinical significance of antibodies. Natalizumab: 2-year results from the AFFIRM study. 15th Annual Meeting of the Neurological Society. Vienna, Austria. Jun. 18-22, 2005. Meeting Poster. P492.

Kaufman; Sharp,"Amplification and expression of sequences cotransfected with a modular dihydrofolate reductase complementary DNA gene," J. Mol. Biol., vol. 159, pp. 601-621 (1982).

Khatri et al., "Plasma Exchange Accelerates the Decline of Serum Natalizumab Concentration in Patients with Multiple Sclerosis: Results of the Natalizumab PLEX Study", Neurology, 70, pp. A227-A228, (2008).

Khatri et al., "Plasma Exchange Accelerates the Decline of Serum Natalizumab Concentration in Patients with Multiple Sclerosis: Results of the Natalizumab PLEX Study", Presentation, (2008).

Khatri et al., "Effect of plasma exchange in accelerating natalizumab clearance and restoring leukocyte function", Neurology vol. 72. No. 5, (Feb. 3, 2009). p. 402-409.

Khatri et al., 60th Annual Meeting of American Academy of Neurology, Chicago, Apr. 2008.

Knowles W A et al., "The JC virus antibody response in serum and cerebrospinal fluid in progressive multifocal leucoencephalopathy.", Clinical and Diagnostic Virology vol. 4, No. 2, Aug. 1995, pp. 183-194.

Koren, Smith E, et al., "Recommendations on risk-based strategies for detection and characterization of antibodies against biotechnology products" Journal of Immunological Methods, vol. 333,Nr:1-2,pp. 1- 9.

Kuus-Reichel et al. "Will immunogenicity limit the Use, Efficacy and the Future Development of therapeutic monoclonal Antibodies?", Clinical and Diagnostic Laboratory Immunology, Minireview, vol. 1, Jul. 1994, pp. 365-372.

Lundkvist et al., "Characterization of anit-natilzumab antibodies in multiple sclerosis patients", Multiple Sclerosis Journal, vol. 19(6), pp. 757-764 (2012).

Major, "Progressive Multifocal Leukoencephalopathy in Patients on Immunomodulatory Therapies", Annu. Rev. Med. 61:35-47 (2010), Aug. 31, 2009, Epub ahead of print.

Merck Manual of Medical Information, Second Home Edition, Edited by Beers et al., pp. 1560-1561 (2003).

Miller D H, "Colloquium C15: Natalizumab (anti-VLA4 antibody) in multiple sclerosis", Journal of Neurochemistry, Wiley Interscience, New York, NY, US, vol. 85, no. Suppl. 1, Jan. 1, 2003, p. 96, C15-04, XP003009634, ISSN: 0022-3042.

Millipore, "Short Guide for Developing Immunochromatographic Test Strip", (1996).

Mire-Sluis et al., Recommendations for the design and optimization of immunoassays used in the detection of host antibodies against biotechnology products. J Immunol Methods. Jun. 2004;289(1-2):1-16.

Montross et al., "Nuclear Assembly of Polyomavirus Capsids in Insect Cells Expressing the Major Capsid Protein VP1", Journal of Virology (Sep. 1991), vol. 65, No. 9, pp. 4991-4998.

Noseworthy, John H. and Kirkpatrick, Peter, "Natalizumab" Nature Reviews Drug Discovery, vol. 4, pp. 101-102 (2005).

Ou et al., "The major capsid protein, VP1, of human JC virus expressed in *Escherichia coli* is able to self-assemble into a capsid-like particle and deliver exogenous DNA into human kidney cells", Journal of General Virology (1999), vol. 80, pp. 39-46.

Padgett et al., "Prevalence of antibodies in human sera against JC virus, an isolate from a case of progressive multifocal leukoencephalopathy", J. Infect. Dis. 127:467-70, 1973.

Piccinni et. al., "Stronger association of drug-induced progressive multifocal leukoencephalopathy (PML) with biological immunomodulating agents", Eur. J. Clin. Pharmacol. 66:199-206, 2010.

Pendley et al., Immunogenicity of therapeutic monoclonal antibodies. Natalizumab: 1-year results from the Sentinel study. Curr Opin Mol Ther. Apr. 2003;5(2):172-9. Review.

Persson et al., "Generation of diverse high-affinity human monoclonal antibodies by repertoire cloning," Proc. Nat. Acad. Sci. USA, vol. 88, pp. 2432-2436 (1991).

Plavina et al., "Anti-JCV antibody index further defines PML risk in natalizumab-treated MS patients", The 27th Annual Meeting of the Corsortium of Multiple Sclerosis Centers Acknowledgements, Accessed March Neurology. Neurology, Warnke C J Neurol Neurosurg Psychiatry Ann Neurol, May 30, 2013 (May 30, 2013), pp. 1736-1742.

Polman et al., A randomized, placebo-controlled trial of natalizumab for relapsing multiple sclerosis. N Engl J Med. Mar. 2, 2006;354(9):899-910.

Postmarket Requirements and Commitments for Tysabri (FDA, Mar. 2017).

Powers et al., "Expression of single-chain Fv-Fc fusions in Pichia pastoris," J Immunol Methods., vol. 251, pp. 123-135 (2001).

Preliminary Report on Patentability for PCT/US10/52172 dated Apr. 11, 2012.

Print-out of the internet website https://www.bio-rad-antibodies.com/tysabri-antibodies-natalizumab.html.

Pulido, R. et al., Functional evidence for three distinct and independently inhibitable adhesion activities mediated by the human integrin VLA-4. Correlation with distinct alpha 4 epitopes. J Biol Chem. Jun. 5, 1991;266(16):10241-5.

Queen et al., "A humanized antibody that binds to the interleukin 2 receptor," Proc Natl Acad Sci U S A., vol. 86, No. 24, pp. 10029-10033 (1989).

Riechmann et al., Nature, (1988), vol. 332, pp. 323-327.

Rispens et al., "Drug interference in immunogenicity assays depends on valency", J of Pharm Biomedical Analysis, vol. 85, pp. 179-185 (2013).

Rollison Dana E et al., "Prediagnostic circulating antibodies to JC and BK human polyomaviruses and risk of non-Hodgkin lymphoma.", Cancer Epidemiology, Biomarkers & Prevention : A Publication of The American Association for Cancer Research, Cosponsored by The American Society of Preventive Oncology Mar. 2006, vol. 15, No. 3, Mar. 2006 (Mar. 2006), pp. 543-550.

Roskos, L.K. et al., Human antiglobulin responses. Measuring Immunity. 2005; Chapter 13:172-186.

Rossman, H.S., "Neutralizing Antibodies to Multiple Sclerosis Treatments", Supplement to Journal of Managed Care Pharmacy, (20040600), vol. 10, No. 3, pp. S12-S18, XP055476759.

Sadiq et al., "JCV detection in multiple sclerosis patients treated with natalizumab," J Neurol (2010) vol. 257, pp. 954-958.

Salunke et al., "Polymorphism in the Assembly of Polyomavirus Capsid Protein VP", Biophys Journal, vol. 56, pp. 887-900, (1989).

Sandborn et al., "Natalizumab Induction of Maintenance Therapy for Crohn's Disease", NEJM, vol. 353(18):1912-1925 (2005).

Sanchez-Madrid, F. et al., VLA-3: a novel polypeptide association within the VLA molecular complex: cell distribution and biochemical characterization. Eur J Immunol. Nov. 1986;16(11):1343-9.

Sands, B.E. et al., Safety and tolerability of natalizumab in patients concurrently receiving infliximab in a phase 2 study of active Crohn's disease. Gastroenterology. Apr. 2004;126:A463.

Sandrock et al., "Risk Stratification for Progressive Multifocal Leukoencephalopathy (PML) in MS Patients: Role of Prior Immunosuppressant Use, Natalizumab-Treatment Duration, and Anti-JCV Antibody Status", Neurology, vol. 76, No. 9, Suppl. 4, Mar. 2011 (Mar. 2011), p. A248, 63rd Annual Meeting of the American Academy of Neurology; Honolulu, HI, USA; Apr. 9-16, 2011.

Sandrock et al., "Risk of Natalizumab-Associated Progressive Multifocal Leukoencephalopathy" 25th Annual Meeting of the Consortium of Multiple Sclerosis Centers, Jun. 1-4, 2011 Montreal, Quebec, Canada.

Sheremata, W.A. et al., A safety and pharmacokinetic study of intravenous natalizumab in patients with MS. Neurology. Mar. 23, 1999;52(5):1072-4.

Sørensen et al., Occurrence of antibodies against natalizumab in relapsing multiple sclerosis patients treated with natalizumab. Mult Scler. Sep. 2011;17(9):1074-8. doi: 10.1177/1352458511404271. Epub Apr. 20, 2011.

Stolt et al., "Seroepidemiology of the human polyomaviruses", Journal of General Virology (2003), vol. 84, pp. 1499-1504.

(56) References Cited

OTHER PUBLICATIONS

Stuve et al., "Potential Risk of Progressive Multifocal Leukoencephalopathy With Natalizumab Therapy", Arch Neurol. vol. 64, (Feb. 2007). P9 169-176.
"Subramanyam, M, 2008. Case study Col. II of the series "Biotechnology: Pharmaceutical Aspects", pp. 173-187".
Subramanyam et al., "Anti-JCV Antibodies Are Consistently Detected Prior to and after PML Diagnosis in Natalizumab-Treated MS Patients", Neurology, vol. 76, No. 9, Suppl. 4, Mar. 2011 (Mar. 2011), pp. A636-A637, 63rd Annual Meeting of the American Academy of Neurology; Honolulu, HI, USA; Apr. 9-16, 2011.
Supplementary European Search Report dated Aug. 30, 2013 for EP 11 73 2315.
Supplementary Partial European Search Report from corresponding European Application No. 12792375.3 dated Jun. 1, 2015.
Takada et al., "The integrins", Genome Biol. 8:215 (2007).
Tempest et al., "Reshaping a human monoclonal antibody to inhibit human respiratory syncytial virus infection in vivo," Biotechnology, vol. 9, pp. 266-271 (1991).
Third Party Observation for European Application No. 14803732.8, dated Dec. 11, 2017.
Third Party Observation for European Application No. Ep 11732315.4 dated Jun. 9, 2015.
Third Party Observation for European Patent Application No. 11732315.4 dated Dec. 10, 2014.
Trampe A. K., et al. "Anti-JC virus antibodies in a large German natalizumab-treated multiple sclerosis cohort." Neurology 78.22 (2012): 1736-1742.
Tubridy N et al., "The effect of anti-[alpha]4 integrin antibody on brain lesion activity in MS," Neurology. 53:466-472 (1999).
Urlaub; Chasin, "Isolation of Chinese Hamster Cell Mutants Deficient in Dihydrofolate Reductase Activity," Proc. Natl. Acad. Sci. USA, vol. 77, pp. 4216-4220 (1980).
"Validierung in der Analytik" by Dr. Stavros Kromidas, Wiley-VCH, Weinheim, 1999, ISBN 3-527-28748-5, pp. 176-181 and 250-251.

Van Assche, "Progressive Multifocal Leukoencephalopathy After Natalizumab Therapy for Crohn's Disease", the New England Journal of Medicine, vol. 353, No. 4, pp. 362-368, (2005).
Vaughan et al., "Human Antibodies with Sub-nanomolar Affinities Isolated from a Large Non-immunized Phage Display Library," Nat Biotechnol. MAR, vol. 14, No. 3, pp. 309-314 (1996).
Verbeeck J et al: "JC viral loads in patients with Crohn's disease treated with immunosuppression: can we screen for elevated risk of progressive multifocal leukoencephalopathy?", Gut vol. 57, No. 10, Oct. 2008.
Verhoeyen et al., "Reshaping human antibodies: grafting an antilysozyme activity," Science, vol. 239, pp. 1534-1536 (1988).
Viscidi, "Serological Cross-Reactivities between Antibodies to Simian Virus 40, BK Virus, and JC Virus Assessed by Virus-Like-Particle-Based Enzyme Immunoassays", Clinical and Diagnostic Laboratory Immunology, vol. 10, No. 2, pp. 278-285, (2003).
Vollmer TL et al., 2004. Multiple Sclerosis. 10:511.
Warnke et al.: "Natalizumab and progressive multifocal leukoencephalopathy: what are the causal factors and can it be avoided?", Archives of Neurology, vol. 67, No. 8, Aug. 1, 2010 (Aug. 1, 2010), pp. 923-930.
Wayback Machine Internet Archive: Capture of the products offered by Maine Biotechnology Services, Inc. in the time from May 10, 2004 to Aug. 13, 2004.
Wayback Machine Internet Archive: Capture of the website of Athena Feb. to Apr. 3, 2005.
Wayback Machine Internet Archive: Captures of the website of Elan from Feb. 10 to Apr. 3, 2005.
Weber T et al: "Analysis of the systemic and intrathecal humoral immune response in progressive multifocal leukoencephalopathy.", The Journal of Infectious Diseases vol. 176, No. 1, Jul. 1997 pp. 250-254.
Wenning, et al., Treatment of Progressive Multifocal Leukoencephalopathy Associated with Natalizumab, N Engl J Med, vol. 361. No. 11. (Sep. 10, 2009), p. 1075-1080.
Wikipedia, "Polyomavirus Capsid Protein (VP1)", Retrieved from the Internet: URL: http://en.wikipedia.org/wiki/Polyomavirus_capsid_protein_(VP1), (2015).
Written Opinion for PCT/US2011/020832 dated Mar. 14, 2011.

* cited by examiner

METHODS AND PRODUCTS FOR EVALUATING AN IMMUNE RESPONSE TO A THERAPEUTIC PROTEIN

RELATED APPLICATIONS

This application is a continuation of U.S. application Ser. No. 15/616,669, filed Jun. 7, 2017, now U.S. Pat. No. 10,705,095, which is a continuation of U.S. application Ser. No. 14/330,619, filed Jul. 14, 2014, now U.S. Pat. No. 9,709,575, which is a continuation of U.S. application Ser. No. 13/242,505, filed Sep. 23, 2011, now U.S. Pat. No. 8,871,449, which is a continuation of U.S. application Ser. No. 11/887,782, filed Mar. 19, 2009, now U.S. Pat. No. 8,124,350, which is a national stage filing under 35 U.S.C. § 371 of international application number PCT/US2006/012493, filed Apr. 4, 2006, which claims priority under 35 U.S.C. § 119 (e) from U.S. provisional application Ser. No. 60/668,404, filed Apr. 4, 2005, the entire content of each of which is incorporated by reference herein.

FIELD OF THE INVENTION

The invention relates to evaluating patients for an immune response to a therapeutic agent, and particularly to a therapeutic protein, for example a VLA-4 binding antibody (e.g. natalizumab).

BACKGROUND OF THE INVENTION

Biologic therapeutics are currently available for treating diseases and disorders such as transplant rejection, leukemia, breast cancer, arthritis, multiple sclerosis, and Crohn's disease; and numerous additional protein-based therapies are in development. Available biologics therapeutics include AMEVIVE® (alefacept), ZEVALIN® (ibritumomab tiuxetan), ORTHOCLONE® (muromonab-CD3), ENBREL® (etanercept), REOPRO® (abciximab), RITUXAN® (rituximab), SIMULECT® (basiliximab), REMICADE® (infliximab), SYNAGIS® (palivizumab), HERCEPTIN® (trastuzumab), ZENAPAX® (daclizumab), CAMPATH® (alemtuzumab), MYLOTARG® (gemtuzumab ozogamicin), HUMIRA® (adalimumab), AVONEX® (Interferon beta-1a), and TYSABRI® (natalizumab). Natalizumab is a humanized monoclonal antibody against α4β1 integrin (VLA-4). Natalizumab binds to the α4 subunit of α4β1 and α4β7 integrins. Natalizumab is useful to treat certain inflammatory diseases and conditions including multiple sclerosis, Crohn's disease, and rheumatoid arthritis.

Because immune responses to biologic therapeutic agents may have clinical consequences, immunogenicity assay development and validation is of great importance in the field of biologic therapeutic agents.

SUMMARY OF THE INVENTION

The invention provides methods and compositions for identifying, monitoring, and/or evaluating an immune response to a therapeutic agent, e.g., a therapeutic protein, e.g., a therapeutic antibody. The fact that a patient develops any antibodies to a therapeutic agent (such as a therapeutic protein or therapeutic antibody) may or may not correlate with a clinical response to the therapeutic agent. Aspects of the invention are based, in part, on the discovery of an unexpected level of antibody response that can be used as a threshold for detecting a clinically significant response to the therapeutic agent. In some embodiments, the threshold level is higher than would have been predicted using a statistical analysis of patients that have not received the therapeutic agent. The clinically significant threshold is generally higher than the lowest detectable level of immune response in a patient. For example, the clinically significant threshold level is generally at least 2 standard deviations above a negative control level, e.g., above a mean pre-treatment level of an untreated patient population. In some embodiments, the higher threshold levels used in methods of the invention result in fewer false positives than would be identified if the threshold level were based on a 5% cutoff (e.g., 1.645 standard deviations above the mean) for immune responses observed in patients that had not received the therapeutic agent. According to aspects of the invention, the presence of a detectable immune response in a patient sample is not clinically significant unless the immune response reaches at least a predetermined threshold level. The invention provides, inter alia, methods of identifying a clinically significant threshold level of antibody response to a therapeutic agent (e.g., a therapeutic protein, e.g., a therapeutic antibody), and methods of identifying patients who have a clinically significant antibody response to a therapeutic agent. The invention, in part, also provides a threshold level with which to identify clinically meaningful antibodies in a subject. According to aspects of the invention, an immune response to a therapeutic agent (e.g., natalizumab) may not be clinically significant (e.g., may not show a significant association with reduced clinical efficacy) unless the magnitude of the immune response reaches a threshold level that can be predetermined (e.g., based on immune responses obtained for different patient groups). Surprisingly, the methods described herein do not rely on comparing samples obtained from each patient before and after treatment, nor do they rely on identifying the mere presence of a detectable immune response to the therapeutic agent. In contrast, methods of the invention, relate to detecting at least a threshold level of an immune response to a therapeutic agent, where the threshold level may be higher than the lowest detectable level of immune response, and wherein the positive results from the assay are clinically meaningful, in part, because the assay avoids false positives that have no associated clinical significance.

Currently, there is no generally applicable technique or standard for detecting a clinically significant antibody response to a therapeutic protein. Different therapeutic proteins may induce different types of antibodies, and the presence of such antibodies may or may not affect the safety, pharmacokinetics, and/or efficacy of a therapeutic protein. Current methods of monitoring a patient's response to a therapeutic antibody typically involve comparing levels of serum antibodies before and after treatment for each patient identifying the presence of any detectable immune response, and evaluating the patient to determine whether the detectable immune response is correlated with any safety, pharmacokinetic, and/or efficacy issues. In contrast, methods of the present invention are useful to identify those patients with clinically significant immune responses by providing screening assays for detecting clinically significant threshold levels of response.

According to the invention, a clinically significant immune response to a therapeutic agent is an antibody response that may affect one or more clinical parameters in a patient, and/or the pharmacokinetics and/or efficacy of the therapeutic agent. Generally, a clinically significant antibody response indicates a diminution of efficacy or lack of efficacy of the therapeutic agent, or an adverse reaction to the therapeutic agent. For example, for multiple sclerosis, a clinically significant antibody response to a therapeutic protein includes one or more of: (a) lack of efficacy or at least 10%, 20%, 30%, 40%, 50%, 60% or more diminution in efficacy of the therapeutic agent to reduce the number, severity or rate of relapse in the patient; (b) lack of efficacy or at least 10%, 20%, 30%, 40%, 50%, 60% or more diminution in efficacy of the therapeutic agent to slow progression of disability in the Expanded Disability Status Scale (EDSS) scale or Multiple Sclerosis Functional Composite (MSFC) scale; (c) lack of efficacy or at least 10%, 20%, 30%, 40%, 50%, 60% or more diminution in efficacy in reducing the number or volume of new or newly enlarging T2 hyperintense lesions or attenuating the increase in T2 hyperintense lesion volume on brain MRI, (d) lack of efficacy or at least 10%, 20%, 30%, 40%, 50%, 60% or more diminution in efficacy in reducing the number or volume of gadolinium-enhancing lesions on brain MRI; (e) lack of efficacy or at least 10%, 20%, 30%, 40%, 50% 60% or more diminution in efficacy in improving visual function; (f) presence of a serious adverse event (e.g., hypersensitivity reaction, e.g., anaphylaxis). With the exception of (f), such responses are evaluated within a specified period of time after administration of the agent, e.g., within 3 months, 6 months, 9 months, or at least one year.

In one aspect, the invention provides methods of identifying a clinically significant threshold level of antibody response to a therapeutic agent (e.g., a therapeutic protein, e.g., a therapeutic antibody). The method includes (a) evaluating the level of anti-agent antibodies in a control population of patients who have a disorder (e.g., determining the mean or median level of anti-agent antibodies in a population of at least 2, 3, 5, 10, 20, 30, 50, 100 or more patients who have a disorder and who have not been treated with a subject therapeutic agent for at least 3 months, 6 months or longer); and (b) selecting a threshold level of at least 2 (e.g., 2.5, 3, 4, 5, or 6) standard deviations above the level of anti-agent antibodies in the control population. The presence of at least the threshold level of anti-agent antibodies in a patient who has been administered the therapeutic agent (the treated patient) correlates with a clinically significant response in the treated patient. Preferably, the same detection reagent (e.g., labeled anti-agent antibody) is used to evaluate the treated patient as is used to identify the level of anti-agent antibodies in the control population. In one embodiment, the therapeutic agent is a therapeutic antibody, e.g., a humanized 21.6 anti-VLA-4 antibody, e.g., natalizumab. In one embodiment, the disorder is multiple sclerosis. In some embodiments, the disorder is an inflammation of the central nervous system (e.g., meningitis, neuromyelitis optica, neurosarcoidosis, CNS vasculitis, encephalitis, or transverse myelitis, in addition to or instead of multiple sclerosis,), a tissue or organ graft rejection or a graft-versus-host disease, an acute CNS injury (e.g., stroke or spinal cord injury); chronic renal disease; allergy (e.g., allergic asthma); type 1 diabetes; an inflammatory bowel disorders (e.g., Crohn's disease, or ulcerative colitis); myasthenia gravis; fibromyalgia; an arthritic disorder (e.g., rheumatoid arthritis or psoriatic arthritis); an inflammatory/immune skin disorder (e.g., psoriasis, vitiligo, dermatitis, or lichen planus); systemic lupus erythematosus; Sjogren's Syndrome; a hematological cancer (e.g., multiple myeloma, leukemia, or lymphoma); a solid cancer such as a sarcoma or a carcinoma (e.g., of the lung, breast, prostate, or brain); or a fibrotic disorder (e.g., pulmonary fibrosis, myelofibrosis, liver cirrhosis, mesangial proliferative glomerulonephritis, crescentic glomerulonephritis, diabetic nephropathy, or renal interstitial fibrosis). In some embodiments, the disorder is a disease that involves modulation of an $\alpha 4\beta 1$ and/or $\alpha 4\beta 7$ subunit.

In another aspect, the invention provides methods of identifying a patient who has a clinically significant antibody response to a therapeutic protein, e.g., a therapeutic antibody. The method includes identifying, in a biological sample obtained from a subject who has a disorder and who has been administered the therapeutic protein, the presence of a threshold level of one or more antibodies that specifically bind to the therapeutic protein, wherein the threshold level is at least 2 (e.g., 2.5, 3, 4, 5, or 6) standard deviations above the level of antibodies that specifically hind to the therapeutic protein in a control population (e.g., a population of patients who have the disorder but have not been administered the therapeutic protein within the last 3 months, 6 months or more). In one embodiment, the therapeutic protein is a therapeutic antibody, e.g., a humanized 21.6 (also referred to as AN100226) anti-VLA-4 antibody, e.g., natalizumab. In one embodiment, the disorder is multiple sclerosis. In some embodiments, the disorder is rheumatoid arthritis. In certain embodiments, the disorder is Crohn's disease. In one embodiment, the method further includes modifying the treatment regimen of a patient who is thus identified as having a clinically significant antibody response to a therapeutic protein.

In one aspect, the invention provides methods and compositions for identifying in a biological sample obtained from a subject the presence of a clinically significant level of one or more antibodies that specifically bind to a therapeutic VLA-4 binding antibody that was administered to the subject. Aspects of the invention include the use of ELISA assays for the detection of levels of induced antibodies that are indicative of a clinically significant immune response in a subject to the administration of a therapeutic VLA-4 binding antibody. In one embodiment, the invention provides methods and kits for identifying clinically significant levels of anti-natalizumab antibodies that are indicative of an immune response to natalizumab in a subject that has received at least one dose of natalizumab In one aspect, the invention provides methods for evaluating and/or modifying a therapeutic regimen based on a subject's immune response to a VLA-4 binding antibody.

According to one aspect of the invention, methods of detecting a clinically significant immune response to a VLA-4 binding antibody in a subject are provided. The methods include determining whether a biological sample from a subject that has been administered a VLA-4 binding antibody contains a clinically significant threshold level of a soluble antibody that binds to the VLA-4 binding antibody, wherein the presence of at least the threshold level of the soluble antibody is indicative of a clinically significant immune response to the VLA-4 binding antibody. In some embodiments, a clinically significant immune response to the VLA-4 binding antibody is indicated by the presence of at least the threshold level of soluble antibody to the VLA-4 binding antibody in at least two biological samples taken from the subject at different time points. In certain embodiments, the time points are separated by at least one month. In some embodiments, at least the threshold level of soluble antibody that binds to the VLA-4 binding antibody is present in two biological samples taken from the subject at two consecutive time points. In some embodiments, a level of soluble antibody that binds to the VLA-4 binding antibody is determined by: determining a level of soluble binding activity to the VLA-4 binding antibody in a first aliquot of the biological sample; and determining whether the soluble binding activity is specific for the VLA-4 binding antibody. In certain embodiments, the specificity of the soluble binding activity is determined in a second aliquot of the biological sample. In some embodiments, a level of soluble antibody that binds to the VLA-4 binding antibody in the biological sample is determined by comparing levels of binding activity to a labeled VLA-4 binding antibody measured in the presence of two or more different amounts of unlabeled VLA-4 binding antibody (e.g., levels measured in the presence of no unlabeled VLA-4 binding antibody may be compared to levels measured in the presence of a competing amount of unlabeled VLA-4 binding antibody). In certain embodiments, a level of soluble antibody that binds to the VLA-4 binding antibody in the biological sample is determined by comparing levels of binding activity to an immobilized VLA-4 binding antibody measured in the presence of two or more different amounts of soluble VLA-4 binding antibody (e.g., levels measured in the presence of no soluble VLA-4 binding antibody may be compared to levels measured in the presence of a competing amount of soluble VLA-4 binding antibody). In some embodiments, a first level of binding activity to a labeled VLA-4 binding antibody measured in the presence of a first amount of unlabeled VLA-4 is compared to a second level of binding activity to a labeled VLA-4 binding antibody measured in the presence of a second amount of unlabeled VLA-4 binding antibody. In some embodiments, the first and second levels of binding activity are determined in first and second aliquots of the biological sample. In certain embodiments, the amount of soluble antibody to the VLA-4 binding antibody is determined using a bridging ELISA assay. In some embodiments, a first level of binding activity to the VLA-4 binding antibody is determined in a first immunoassay for a first aliquot of the biological sample, and a second level of binding activity to the VLA-4 binding antibody is determined in a second immunoassay for a second aliquot of the biological sample, wherein the second immunoassay is spiked with a greater amount of unlabeled soluble VLA-4 binding antibody than the first immunoassay, and wherein the presence in the biological sample of at least a threshold level of soluble antibody to the VLA-4 binding antibody is indicated if the first level of binding activity is greater than a reference level and the second level of binding activity is less than a predetermined percentage of the first level of binding activity. In certain embodiments, the reference level is a level of binding activity measured for a reference amount of soluble antibody to the VLA-4 binding antibody. In some embodiments, the reference amount is about 500 ng/ml (e.g., in a serum sample) of a soluble antibody to the VLA-4 binding antibody. For example, the reference amount may be between about 400 ng/ml and about 600 ng/ml (e.g., about 400 ng/ml, about 425 ng/ml, about 450 ng/ml, about 475 ng/ml, about 500 ng/ml, about 525 ng/ml, about 550 ng/ml, about 575 ng/ml, or about 600 ng/ml). It should be appreciated that the reference level of binding activity that corresponds to the reference amount may be measured in a diluted sample (for example, a sample that corresponds to a 10 fold dilution and contains from about 40 ng/ml to about 60 ng/ml, e.g., about 50 ng/ml, of a soluble antibody to the VLA-4 binding antibody). A reference level of binding activity in an assay may be provided by any predetermined amount of soluble antibody to the VLA-4 binding antibody corresponding to an appropriate dilution of the reference amount. In certain embodiments, the VLA-4 binding antibody is a humanized murine monoclonal antibody to VLA-4. In some embodiments, the VLA-4 binding antibody is a humanized form of murine antibody mAb 21.6, (e.g., AN100226). In some embodiments, the VLA-4 binding antibody is natalizumab. In some embodiments, the soluble antibody to the VLA-4 binding antibody is a reference antibody that binds to natalizumab with high affinity. In some embodiments, the reference antibody blocks the interaction between natalizumab and VLA-4. In certain embodiments, the first and second immunoassays are bridging ELISA assays. In some embodiments, the first and second assays comprise an immobilized unlabeled VLA-4 binding antibody and a soluble labeled VLA-4 binding antibody, wherein the soluble labeled VLA-4 binding antibody is labeled with an enzyme, a fluorescent marker, a biotin marker (e.g., the VLA-4 binding antibody may be biotinylated), or a radioactive marker. In some embodiments, the first and second immunoassays are conducted in parallel reaction volumes on a single reaction substrate. In some embodiments, the biological sample is a serum sample. In certain embodiments, the subject is a human patient. In some embodiments, the patient has multiple sclerosis. In some embodiments, the patient has rheumatoid arthritis. In certain embodiments, the patient has Crohn's disease. In some embodiments, the time points of at least two or more biological samples obtained the subject are separated by at least 15 days, 30 days, 45 days, 60 days, 90 days, or more. In certain embodiments, the method also includes selecting a therapeutic regimen for the subject if a clinically significant threshold level of a soluble antibody that binds to the VLA-4 binding antibody is detected in at least two biological samples obtained from the subject. In some embodiments, selecting a therapeutic regimen includes evaluating a current therapy of the subject, determining a new therapy for the subject, modifying a current therapy of the subject, or stopping a current therapy of the subject. In some embodiments, a current therapy includes administering the VLA-4 binding antibody to the subject.

According to another aspect of the invention, methods of selecting a therapeutic regimen for a subject are provided. The methods include assaying a subject who has been administered a VLA-4 binding antibody for the presence of a positive immune response to the VLA-4 binding antibody at first and second time points, selecting a therapeutic regimen for the subject based on the assay results at the first and second time points, wherein the presence of a positive immune response at a point in time is indicated by the presence of at least a clinically significant threshold amount of binding activity in a biological sample obtained from the subject at the point in time. In some embodiments, the first and second time points are separated by a clinically significant time period. In certain embodiments, the clinically significant time period is at least 30 days. In some embodiments, VLA-4 binding antibody therapy is continued if a negative immune response is detected at the second time point. In some embodiments, a therapy other than VLA-4 binding antibody therapy is selected if a positive immune response is detected at both the first and second time points. In some embodiments, the subject has multiple sclerosis. In certain embodiments, the subject has Crohn's disease. In some embodiments, the subject has rheumatoid arthritis.

According to yet another aspect of the invention, methods of selecting a therapeutic regimen for a subject are provided. The methods include detecting the presence of a clinically significant immune response to a VLA-4 binding antibody in at least two biological samples obtained from a subject, wherein the subject has been administered a VLA-4 binding antibody and the at least two biological samples are obtained from the subject at times separated by at least a clinically significant time interval, and selecting a therapeutic regimen based on the detection of a clinically significant immune response to the VLA-4 antibody in the subject at the times when the at least two biological samples are obtained from the subject. In some embodiments, the clinically significant interval separating the times at which the samples are obtained from the subject is at least 15 days, 30 days, 45 days, 60 days, 90 days, or longer. In certain embodiments, selecting a therapeutic regimen includes evaluating a current therapy of the subject, determining a new therapy for the subject, modifying a current therapy of the subject, or stopping a current therapy of the subject. In some embodiments, a current therapy includes administering the VLA-4 antibody to the subject. In some embodiments, detecting the presence of a clinically significant immune response to a VLA-4 binding antibody comprises, determining whether a biological sample obtained from a subject that has been administered a VLA-4 binding antibody contains a threshold level of a soluble antibody that binds to the VLA-4 binding antibody, wherein the presence of at least the threshold level of the soluble antibody is indicative of a clinically significant immune response to the VLA-4 binding antibody. In certain embodiments, at least the threshold level of soluble antibody that binds to the VLA-4 binding antibody is present in two biological samples taken from the subject at two consecutive time points. In some embodiments, a level of soluble antibody that binds to the VLA-4 binding antibody is determined by: determining a level of soluble binding activity to the VLA-4 binding antibody in a first aliquot of the biological sample and determining whether the soluble binding activity is specific for the VLA-4 binding antibody. In some embodiments, the specificity of the soluble binding activity is determined in a second aliquot of the same biological sample. In certain embodiments, a level of soluble antibody that binds to the VLA-4 binding antibody in the biological sample is determined by comparing levels of binding activity to a labeled VLA-4 binding antibody measured in the presence of two or more different amounts of unlabeled VLA-4 binding antibody (e.g., levels measured in the presence of no unlabeled VLA-4 binding antibody may be compared to levels measured in the presence of a competing amount of unlabeled VLA-4 binding antibody). In some embodiments, a level of soluble antibody that binds to the VLA-4 binding antibody in the biological sample is determined by comparing levels of binding activity to an immobilized VLA-4 binding antibody measured in the presence of two or more different amounts of soluble VLA-4 binding antibody (e.g., levels measured in the presence of no soluble VLA-4 binding antibody may be compared to levels measured in the presence of a competing amount of soluble VLA-4 binding antibody). In some embodiments, a first level of binding activity to a labeled VLA-4 binding antibody measured in the presence of a first amount of unlabeled VLA-4 is compared to a second level of binding activity to a labeled VLA-4 binding antibody measured in the presence of a second amount of unlabeled VLA-4 binding antibody. In certain embodiments, the first and second levels of binding activity are determined in first and second aliquots of the same biological sample. In some embodiments, the amount of soluble antibody to the VLA-4 binding antibody is determined using a bridging ELISA assay. In some embodiments, a first level of binding activity to the VLA-4 binding antibody is determined in a first immunoassay for a first aliquot of the biological sample, and a second level of binding activity to the VLA-4 binding antibody is determined in a second immunoassay for a second aliquot of the biological sample, wherein the second immunoassay is spiked with a greater amount of unlabeled soluble VLA-4 binding antibody than the first immunoassay, and wherein the presence in the biological sample of at least a threshold level of soluble antibody to the VLA-4 binding antibody is indicated if the first level of binding activity is greater than a reference level and the second level of binding activity is less than a predetermined percentage of the first level of binding activity. In some embodiments, the reference level is a level of binding activity measured for a reference amount of soluble antibody to the VLA-4 binding antibody. In certain embodiments, the reference amount is about 500 ng. In some embodiments, the VLA-4 binding antibody is a humanized murine monoclonal antibody to VLA-4. In some embodiments, the VLA-4 binding antibody is a humanized form of murine antibody mAb 21.6. In some embodiments, the VLA-4 binding antibody is natalizumab. In certain embodiments, the first and second immunoassays are bridging ELISA assays. In some embodiments, the first and second assays comprise an immobilized unlabeled VLA-4 binding antibody and a soluble labeled VLA-4 binding antibody, wherein the soluble labeled VLA-4 binding antibody is labeled with an enzyme, a fluorescent marker, a biotin marker (e.g., the VLA-4 binding antibody may be biotinylated), or a radioactive marker. In some embodiments, the first and second immunoassays are conducted in parallel reaction volumes on a single reaction substrate (e.g., in separate wells of a multi-well plate). In certain embodiments, the biological sample is a serum sample. In some embodiments, the subject is a human patient. In some embodiments, the patient has multiple sclerosis. In some embodiments, the patient has rheumatoid arthritis. In certain embodiments, the patient has Crohn's disease.

According to another aspect of the invention, methods of identifying a clinically significant threshold level of antibody response to a protein therapeutic agent for a patient who has a disorder are provided. The methods includes (a) evaluating the level of anti-agent antibodies in a control population of patients who have the disorder and who have not been treated with the agent and (b) selecting a level at least 2 standard deviations above the level of anti-agent antibodies in the control population as a clinically significant threshold level of antibody response for patients who have the disorder and are treated with the agent. In some embodiments, the protein therapeutic agent is a therapeutic antibody or antigen-binding fragment thereof.

According to yet another aspect of the invention, methods of identifying a patient who has a clinically significant antibody response to a therapeutic protein are provided. The methods include assaying, in a biological sample obtained from a patient who has a disorder and who has been administered the therapeutic protein, for the presence of a threshold level of antibodies that specifically bind to the therapeutic protein, wherein the threshold level is at least 2 standard deviations above the level of antibodies that specifically bind to the therapeutic protein in a control untreated population of patients who have the disorder. In some embodiments, the therapeutic protein is a therapeutic antibody or antigen-binding fragment thereof. Accordingly aspects of the invention provide methods of detecting a clinically significant immune responses to a VLA-4 binding antibody in a subject, by determining whether a biological sample from a subject that has been administered a VLA-4 binding antibody contains a threshold level of a soluble antibody that binds to the VLA-4 binding antibody, wherein the presence of at least the threshold level of the soluble antibody is indicative of a clinically significant immune response to the VLA-4 binding antibody.

Each of the limitations of the invention can encompass various embodiments of the invention. It is, therefore anticipated that each of the limitations of the invention involving any one element or combinations of elements can be included in each aspect of the invention.

DETAILED DESCRIPTION OF THE INVENTION

Figure 1:
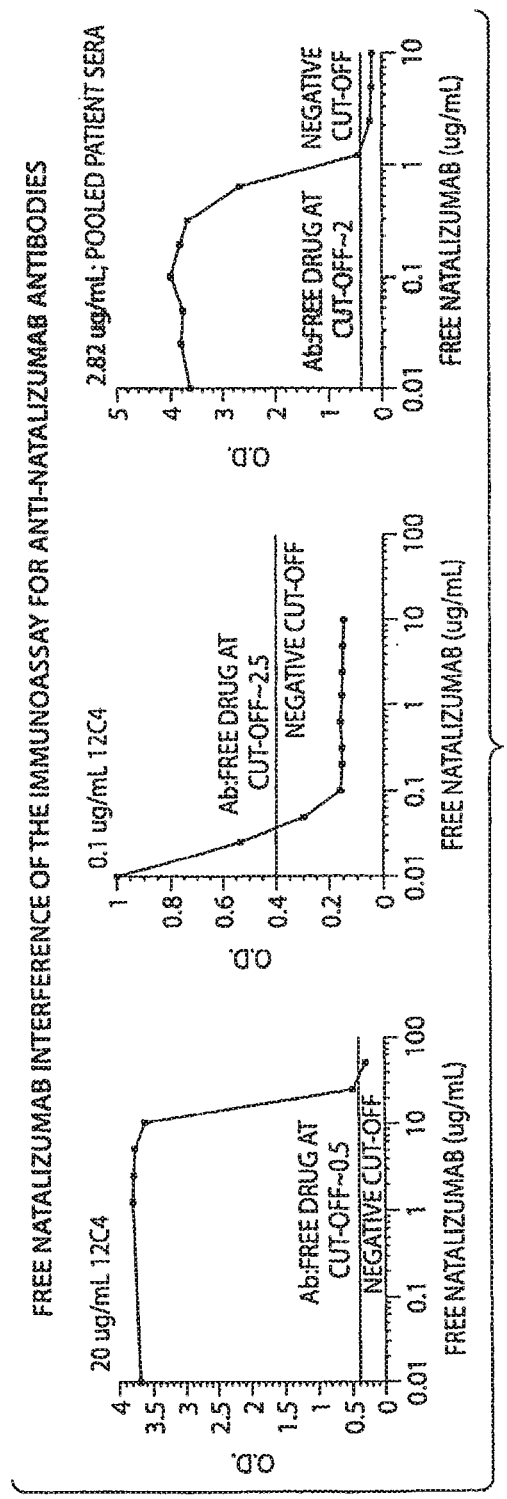
FIG. 1 illustrates the interference of free natalizumab in an immunoassay.

The present invention relates, in part, to methods, compositions, and kits for detecting and monitoring an immune response to a therapeutic protein (e.g., a therapeutic antibody) that is administered to a subject. In one aspect, the invention provides methods for identifying patients with a clinically significant immune response to a therapeutic antibody. According to the invention, the presence of a detectable immune response is not clinically significant unless the immune response reaches a clinically significant threshold level. For example, in clinical studies of natalizumab, a clinically significant threshold level of immune response was surprisingly more than 1.645 standard deviations (e.g., at more than about 2 standard deviations) above a control level of immune response observed for subjects that have not received the therapeutic agent.

Certain aspects of the invention relate to methods for detecting a clinically significant immune response against a therapeutic VLA-4 binding antibody that is administered to a subject. Aspects of the invention are particularly useful for detecting and monitoring immune responses in a subject who has received at least one dose (e.g., one therapeutic dose) of a VLA-4 binding antibody. Aspects of the invention include identifying and/or monitoring a subject with a clinically significant immune response to a therapeutic VLA-4 binding antibody, evaluating the immune response, and/or determining an appropriate clinical treatment (e.g., a particular therapeutic regimen) based on the nature and/or extent of the immune response. Information about a subject's response to the administration of a VLA-4 binding antibody may be used to adjust, design, and/or optimize a therapeutic regimen for the subject. Accordingly, one aspect of the invention relates to identifying a subject who has a clinically significant immune response to a therapeutic VLA-4 binding antibody. Another aspect of the invention relates to monitoring a subject's immune response to a therapeutic VLA-4 binding antibody. A further aspect of the invention relates to determining appropriate therapeutic strategies to treat certain diseases (e.g., multiple sclerosis, Crohn's disease, or rheumatoid arthritis, etc.) based on a subject's immune response to a therapeutic VLA-4 binding antibody.

VLA-4 binding antibodies may be used to treat a number of diseases and disorders associated with inflammation. Such disorders include, e.g., inflammation of the central nervous system (e.g., in addition to multiple sclerosis, meningitis, neuromyelitis optica, neurosarcoidosis, CNS vasculitis, encephalitis, and transverse myelitis), tissue or organ graft rejection or graft-versus-host disease, acute CNS injury, e.g., stroke or spinal cord injury; chronic renal disease; allergy, e.g., allergic asthma; type 1 diabetes; inflammatory bowel disorders, e.g., Crohn's disease, ulcerative colitis; myasthenia gravis; fibromyalgia; arthritic disorders, e.g., rheumatoid arthritis, psoriatic arthritis; inflammatory/immune skin disorders, e.g., psoriasis, vitiligo, dermatitis, lichen planus; systemic lupus erythematosus; Sjogren's Syndrome; hematological cancers, e.g., multiple myeloma, leukemia, lymphoma; solid cancers, e.g., sarcomas or carcinomas, e.g., of the lung, breast, prostate, brain; and fibrotic disorders, e.g., pulmonary fibrosis, myelofibrosis, liver cirrhosis, mesangial proliferative glomerulonephritis, crescentic glomerulonephritis, diabetic nephropathy, and renal interstitial fibrosis. In some embodiments, the disorder is a disease effected by modulation of an $\alpha 4\beta 1$ or/an $\alpha 4\beta 7$ subunit.

In one embodiment, a VLA-4 binding antibody is a humanized version of murine mAb 21.6, e.g., natalizumab. Accordingly, aspects of the invention relate to evaluating a subject's response to natalizumab and determining appropriate treatments for multiple sclerosis and other inflammatory conditions or diseases that can be treated with natalizumab.

The invention relates in part to identifying an immune response to a VLA-4 binding antibody (e.g., a humanized version of murine mAb 21.6, such as natalizumab, or AN100226) in a subject, and determining whether the response is clinically significant.

As used herein, "identifying" a subject with an immune response means detecting or diagnosing the presence of an immune response in a subject. Accordingly, identifying a subject with a clinically significant immune response means detecting or diagnosing the presence of a clinically significant immune response in a subject.

As used herein, a "clinically significant threshold" for an antibody response to a therapeutic protein is at least 2 standard deviations above a control reference level. In one embodiment, the threshold level for a clinically significant immune response to a therapeutic protein may be between 3 and 6 (e.g., about 4 or 5) standard deviations above a control level. The control level may be a mean or median level of binding activity that is present in a patient population (e.g., a population of subjects with a disease or condition such as multiple sclerosis, Crohn's disease, or rheumatoid arthritis) before exposure to the therapeutic protein. In one embodiment, a clinically significant threshold for anti-natalizumab antibodies is 500 ng/ml of patient sera (e.g., a 50 ng/ml threshold in an assay of 10-fold diluted serum).

As used herein, an immune response is an immunogenic response to a therapeutic protein characterized by increased levels in the subject of one or more antibodies that bind the protein. Thus, an immune response may be characterized by the induction of increased levels of soluble antibodies that recognize (e.g., specifically recognize) and bind to the protein, e.g., a VLA-4 binding antibody (e.g. natalizumab). A typical immune response is polyclonal and may include antibodies with different affinities (and therefore different degrees of specificity) for the therapeutic protein. Accordingly, methods of the invention may involve detecting the presence in a subject of one or more induced antibodies that bind to a therapeutic protein (e.g., a VLA-4 binding antibody) that was administered to the subject. In some embodiments, the induced antibodies may be detected as soluble antibodies that are present in a biological sample (e.g., a serum sample).

Aspects of the invention relate to assays for detecting a clinically significant threshold level of binding activity in a biological sample obtained from a patient. The threshold level represents a level below which any detectable binding activity is considered not to be clinically significant. As used herein, binding activity refers to the detected amount of binding to a therapeutic protein in a biological sample. As described herein, the presence of binding activity in a biological sample may reflect a polyclonal response to the administration of a therapeutic protein. Accordingly, the amount of binding may reflect an aggregate of binding by different antibodies with different affinities for the protein. In certain embodiments, the binding activity is further analyzed to determine with greater confidence whether the level of binding is due to the presence of specific antibodies against the therapeutic protein or due to other factors such as rheumatoid factors. The specificity of a binding activity may be evaluated in competition assays as described herein.

In one aspect of the invention, a subject is identified as a positive (i.e., as having a clinically significant immune response to a therapeutic protein) only if one or more samples obtained from the subject test positive in an assay of the invention. A positive test result is determined when a sample obtained from a subject contains at least a clinically significant threshold level of binding activity for the therapeutic protein, e.g., VLA-4 binding antibody. Surprisingly, the presence of any detectable immune response to a therapeutic antibody is not clinically significant. According to the invention, methods based on screening patients to detect any level of immune response to a therapeutic antibody identify many false positive patients, resulting in unnecessary additional clinical monitoring and potential anxiety for patients who do not have a clinically significant immune response. For example, an excessive number of false positives are detected when patients are identified as positive based on an immune response to a therapeutic antibody that is greater than 1.645 standard deviations above a mean level of binding activity present in subjects that have not received the therapeutic antibody. According to the invention, the theoretical 5% false positive rate using a 1.645 standard deviation cut-off is an underestimate of the number of false positives, because the 5% represents the rate of false-detection of any immune response and not the rate of false-positives for a clinically significant immune response. Surprisingly, by raising the cut-off level (the level below which a response is considered to be negative) to higher than 1.645 standard deviations above a control reference level, the number of false positives is reduced without affecting the identification of subjects with clinically significant immune responses. It should be appreciated that the threshold should be set at a level that results in acceptable detection rates of patients with a clinically significant immune response. Therefore, even though the clinically significant threshold should be set at more than 1.645 standard deviations above a pre-immune reference level, the threshold should not be set so high as to reduce the detection efficiency of actual positives.

In one aspect of the invention, a subject's immune response may be classified as negative if samples obtained from the subject do not test positive in an assay of the invention, e.g., they do not reach the clinically significant threshold level of antibody response. In contrast, if a subject is identified as positive based on a positive level (a level at or above a clinically significant threshold level) of binding activity in a single assay, the patient may be either a "transient" or a "persistent" positive. A transient positive is a patient who has a positive immune response to the therapeutic antibody for a specified period of time after which the patient becomes negative. In contrast, a persistent positive is a patient who is positive for clinically significant levels of immune response for greater than a specified period of time. It should be appreciated that transient and persistent are relative terms. Accordingly, a patient may be classified initially as persistent if the patient tests positive for an immune response at two or more time points (e.g., at 3, 4, 5, 6, 7, 8, 9, 10 or more time points) separated by clinically significant time intervals. However, the patient subsequently may be reclassified as transient if the patient tests negative for an immune response in a subsequent assay. Clinically significant time intervals may be at least one week, one month, one year, or longer. For example, the threshold time interval may be between 30 and 180 days, about 60 days, about 42 days, etc. The presence of a transient immune response may be indicative of a transient reduction in therapeutic efficacy. The presence of a persistent immune response may be indicative of a persistently reduced therapeutic efficacy. Accordingly, the presence of a transient or persistent immune response may be clinically relevant and may affect the nature of a therapeutic regimen in a subject that is identified as transiently positive or persistently positive. A persistent immune response may necessitate a modification of the subject's therapeutic regimen.

As used herein, the term "therapeutic regimen" means a course of treatment for a subject. A therapeutic regimen may include administration of pharmaceutical agent(s) and/or application of a therapy. The selection of a regimen may include selection of dose amount, dose timing, dose frequency, duration of treatment, combination therapies with one or more pharmaceutical agents or therapies, and any other aspects of treatment decision making that are used by those of skill in the medical and therapeutic arts. A therapeutic regimen also may include the use of therapies such as procedures or devices that are administered to or used on a subject for the prevention or treatment of a disease or disorder. Examples of therapeutic procedures, although not intended to be limiting, include the use of medical devices or surgery. Accordingly, determining or altering a VLA-4 binding antibody therapeutic regimen may involve determining or altering the dose amount of therapeutic VLA-4 binding antibody that is administered to a subject, the frequency of administration, the route of administration, the duration of the treatment (e.g., the number of doses that are administered), whether or not to combine a VLA-4 binding antibody treatment with one or more additional treatments, whether to discontinue a VLA-4 binding antibody treatment, whether to use a different VLA-4 binding antibody, and/or whether to use a combination of VLA-4 binding antibodies, etc. In one embodiment, the invention may involve determining whether to use a therapeutic alternative to a VLA-4 binding antibody, e.g., whether to use beta interferon.

Aspects of the invention relate to detecting and/or monitoring an immune response to a VLA-4 binding antibody in a human (e.g., a human patient). Accordingly, as used herein, a subject may be a human subject. A subject may be a human patient that has an inflammatory disease or condition. A subject may be a patient that has received at least one dose of a VLA-4 binding antibody (e.g., natalizumab). A subject may be a patient that is being (or was) treated chronically with a VLA-4 binding antibody (e.g., natalizumab). A subject may be a patient that is being (or was) treated repeatedly with a VLA-4 binding antibody (e.g., natalizumab). As used herein, a chronic treatment may involve administering a VLA-4 binding antibody over an extended period of time (e.g., to control or manage symptoms of an inflammatory disease or condition during the time period). In contrast, a repeated treatment may involve repeating a course of treatment (e.g., a period of administration) with a VLA-4 binding antibody when necessary (e.g., to treat symptoms of an inflammatory disease when they worsen or "flare up"). In one embodiment, a patient is considered to be undergoing a repeated treatment when the subject is re-treated with a therapeutic VLA-4 binding antibody for the first time. It will be understood by those of ordinary skill in the art that a subject may also undergo or have undergone treatments with therapies or procedures in combination with or separate from treatment with a VLA-4 binding antibody. It should be appreciated that aspects of the invention are not limited to human subjects. Accordingly, a subject may be a non-human primate, cow, horse, pig, sheep, goat, dog, cat, rodent, or other non-human subject.

Identifying and Monitoring an Immune Response

In one aspect, the invention involves identifying and/or monitoring an immune response to a VLA-4 binding antibody in a subject. In certain embodiments, the identification and/or monitoring is performed by assaying a biological sample obtained from the subject, preferably blood, for the presence of induced antibodies that bind to the administered VLA-4 binding antibody as described herein.

In one aspect of the invention, a qualitative assay is performed on a biological sample obtained from a subject, and the presence of an immune response is identified if the biological sample contains antibodies against the VLA-4 binding antibody in an amount greater than a threshold amount. In one embodiment, a threshold amount is an amount above which an immune response is identified as being clinically relevant, e.g., the threshold level is determined as described herein. A clinically relevant immune response may have clinical implications, e.g., it indicates that the subject should be evaluated to determine whether the dosage of the administered VLA-4 binding antibody should be modified, to determine whether other physiological parameters of the patient should be monitored, to determine whether a further assay for an immune response should be performed, or to determine whether any alternative or additional steps should be taken to treat or monitor the subject, etc. A clinically relevant immune response may be evaluated along with one or more other factors. It should be appreciated that the identification of a clinically relevant immune response does not, by itself, require that a change be made to the subject's therapy or treatment regimen.

In another aspect of the invention, a quantitative assay may be performed on a biological sample to quantify the amount of antibodies (e.g., the antibody titer) against a VLA-4 binding antibody that was administered to a subject. Quantitative results also may be analyzed to determine whether an immune response is above a clinically significant threshold level.

According to the invention, an immune response against a VLA-4 binding antibody (e.g., natalizumab) may be assessed in a subject over time by performing assays on samples obtained at different time points from the subject. The multiple-assessment strategy permits monitoring of a subject's immune response to the VLA-4 binding antibody and may allow the therapeutic VLA-4 binding antibody regimen to be individually tailored to the subject's therapeutic needs. For example, a sample may be obtained from a subject, tested for an immune response to the VLA-4 binding antibody that has been administered to the subject, and at a second, subsequent time, another sample may be obtained from the subject and similarly tested. Detection and confirmation of the presence of an antibody response in a subject's samples over time by sequential determinations at predetermined time intervals permits monitoring of an immune response to a therapeutic VLA-4 binding antibody treatment. The detection and monitoring of an immune response to an administered VLA-4 binding antibody also allows adjustment in the overall treatment of the subject, for example by adjusting (e.g., modifying or suspending) the VLA-4 binding antibody treatment and/or by adjusting additional therapies (e.g., therapies that modulate the immune response of the subject).

The selection or adjustment of a therapeutic regimen may be based on a determination of a clinically significant immune response to a VLA-4 binding antibody in at least two biological samples obtained at different times from a subject who has been administered a VLA-4 binding antibody. The determination of a subject's clinically significant immune response to the VLA-4 binding antibody may indicate that initiating, continuing, adjusting, or stopping administration of a specific pharmaceutical agent and/or therapy to the subject would be beneficial. For example, the determination of a clinically significant immune response to a VLA-4 binding antibody in at least two biological samples obtained from a subject may be the basis for altering the dose of a pharmaceutical agent that is administered to the subject as part of a current therapeutic regimen. The treatment may be changed to include additional pharmaceutical agents or therapies or to lower or raise the dose of a currently administered agent or therapy. For example, the identification of an immune response to a VLA-4 binding antibody in a subject may suggest initiating or continuing a treatment with an immunosuppressive pharmaceutical agent, etc. In some embodiments, an initial therapeutic regimen may be selected based on the determination of an initial immune response to a VLA-4 binding antibody in a single biological sample obtained from a subject who has been treated with a VLA-4 binding antibody. Following the selection and administration of a selected therapeutic regimen, a subsequent determination of an immune response to a VLA-4 binding antibody in one or more subsequent biological samples obtained from the subject may be made and may provide a basis for adjusting the therapeutic regimen.

The determination of a clinically significant immune response to a VLA-4 binding antibody in two or more biological samples obtained from a subject at different time points can be compared to evaluate or measure the onset, progression, or regression of an immune response in the subject to the VLA-4 binding antibody therapy. Onset of an immune response to a VLA-4 binding antibody in a subject may be characterized by increased level(s) of at least one antibody that binds to a VLA-4 binding antibody, and may be accompanied by the onset of one or more physiological changes or symptoms in the subject. Progression of an immune response to a therapeutic VLA-4 binding antibody may be characterized by a further increase in the level of the at least one antibody that binds to the therapeutic VLA-4 binding antibody. However, the progression of an immune response may involve an increase in the level(s) of at least one additional antibody, and/or a decrease in the level of at least one of the antibodies that increased with the onset of the immune response. For example, an initial immune response may be predominantly an IgM response. As the immune response progresses, the predominant antibodies may switch from IgM to IgG antibodies. Progression of an immune response also may be accompanied by a progression (e.g., an increase, decrease, or modification) of one or more of the initial physiological changes or symptoms or the onset of one or more additional physiological changes or symptoms. Regression of an immune response in a subject to a therapeutic VLA-4 binding antibody may be characterized by a decrease in the level(s) of one or more antibodies that bind to the therapeutic VLA-4 binding antibody. The regression of an immune response also may be accompanied by a decrease of certain physiological changes or symptoms. However, it should be appreciated that onset, progression, and/or regression of an immune response to a therapeutic VLA-4 binding antibody may be clinically asymptomatic, other than the detectable changes in antibody levels.

Progression and regression of a clinically significant immune response to a VLA-4 binding antibody may generally be indicated by the increase or decrease, respectively, of the level of an antibody that binds a VLA-4 binding antibody in a subject's samples over time. For example, if no antibody, or a subclinically significant level of an antibody, that specifically binds a VLA-4 binding antibody is determined to be present in a first sample from a subject and a clinically significant threshold of antibodies that specifically bind a VLA-4 binding antibody is determined to be present in a second or subsequent sample from the subject, it may indicate the onset of an immune response to the VLA-4 binding antibody in the subject. Progression of an immune response to a VLA-4 binding antibody in a subject may be indicated by the presence of a higher level of an antibody that specifically binds a VLA-4 binding antibody in a second or subsequent sample from a subject compared to the level present in the initial or previous sample from the subject. Regression of an immune response to a VLA-4 binding antibody may be indicated by the presence of a lower level of an antibody that specifically binds a VLA-4 binding antibody in a second or subsequent sample from a subject compared to the level present in the initial or previous sample from the subject.

In one aspect of the invention, an immune response may be categorized as either positive or negative based on whether a level of antibodies against a therapeutic VLA-4 binding antibody is above a predetermined clinically significant threshold. In some embodiments, a clinically significant threshold is more than 1.645 (e.g. more than 2, 3, 4, 5, or 6) standard deviations above a mean level of binding activity measured in pre-immune subjects (i.e., subjects who have not received any dose of therapeutic VLA-4 antibody). In some embodiments, the subjects are healthy subjects and in certain embodiments, the subjects are diseased patients (e.g., patients with multiple sclerosis, Crohn's disease, or rheumatoid arthritis). In one embodiment, the threshold level is >0.5 micrograms/ml serum. In some embodiments, the threshold level is equal to about 0.5 micrograms/ml serum.

In one embodiment, subjects who have been administered a VLA-4 binding antibody may be categorized as falling into one of at least three categories. One category, referred to herein as "negative", includes subjects in which binding activities are at or below clinically significant threshold levels (e.g., a subject in which antibodies to a VLA-4 binding antibody are not detected at a concentration of at least about 500 ng/ml in a biological sample (e.g., serum) obtained from the subject). A second category, referred to herein as "transient positive" includes subjects in which binding activities are detected above a threshold level only a limited number of times, e.g., at one, two, three, four, five points in time (e.g., antibodies to a VLA-4 binding antibody are not detected at a subsequent time point separated by at least 30 days from the last time point). A third category, referred to herein as "persistent positive" includes subjects in which binding activities are detected above a threshold level a predetermined number of times, e.g., at two, three, four, five, six, seven or more time points separated by a minimum threshold time interval (e.g., a subject in which antibodies to a VLA-4 binding antibody are detected at a concentration of at least about 500 ng/ml in two three, four, five, six, seven or more biological samples obtained from the subject at time points separated by at least a threshold interval). In some embodiments, the threshold interval is at least about 10, 20, 30, 40, 50, 60, 70, 80, 90, or more days. Patients who are "persistent positive" may have a loss of efficacy from VLA-4 antibody therapy, while "transient positive" patients have full efficacy restored after only a temporary diminution in efficacy.

It should be appreciated that a negative subject may become a transient positive. And either one may become a persistent positive if a positive immune response develops and persists for a specified number of time points, e.g., at least two time points.

In one embodiment, a therapy may be changed based on a determination of a single positive result. In another embodiment, a therapy may be changed based upon a determination that a subject is a transient positive subject. In yet another embodiment, a therapy may be changed based upon a determination that a subject is a persistent positive subject.

As discussed above, it should be appreciated that the terms transient and persistent are relative terms, and that a patient that seems to be persistently positive may become negative at a later time. Accordingly, patients with positive responses should be monitored regularly to evaluate the persistence of the positive response, the effectiveness of the therapy, and/or the presence of other clinical manifestations of a positive immune response.

According to the invention, the risk of a reduction in therapeutic efficacy (e.g., the risk of a relapse) increases with the length of time that a positive immune response persists. Accordingly, in one aspect of the invention, the number of times that a patient tests positive is less important than the length of time over which the patient remains positive. In one embodiment, a patient may be identified as being at risk of a reduction in therapeutic efficacy (e.g., at risk of a relapse) if a positive result is detected within 3 months of the first administration of a therapeutic VLA-4 binding antibody. In one embodiment, this risk increases if the positive immune response persists for 3-6 months, and further increases if the positive immune response persists for 6-9 months, and yet further increases with persistence for 9-12 months after the first administration of the therapeutic VLA-4 binding antibody. It should be appreciated that persistence for more than one year even further increases the probability of a relapse. Accordingly, different therapeutic regimens may be appropriate for a patient with a persistently positive immune response. However, it should be appreciated that even in the presence of a persistently positive immune response, a therapeutic antibody therapy need not be discontinued unless it becomes ineffective (e.g., a loss of substantially all efficacy) or causes other negative clinical manifestations.

In some embodiments, treatment with a therapeutic VLA-4 binding antibody may be discontinued if the treatment is ineffective or is losing is effectiveness in a patient that has a below-threshold level of immune response. A lack of efficacy (or a reduction in efficacy) in the absence of a clinically significant immune response may indicate that the ineffectiveness of the treatment is due to one or more factors other than a patient immune response to the therapeutic agent. A patient will not be a transient positive if no positive response is detected. Accordingly, alternative treatment may be considered.

It should be appreciated that binding activities or antibody levels may be compared to pre-immune activities or levels (i.e., measured before the administration of the first dose of VLA-4 binding antibody). However, a comparison to a pre-immune amount is not necessary as discussed herein, because a positive immune response may be identified when a clinically significant threshold (or above threshold) amount of binding activity or antibody levels are present in a patient sample.

Assays and Detection Methods

According to aspects of the invention, a threshold amount of an antibody response is assayed for. As discussed herein, a qualitative assay may be performed. Alternatively, a quantitative assay may be performed and in one embodiment, the quantitative data may be translated into a qualitative output (e.g., whether the amount of antibody is greater than a threshold amount).

Any suitable method for detecting an amount of antibody or binding activity may be used to determine whether it is at least a threshold amount or activity. Detection assays may include any known immunodetection methods for detecting, confirming, binding, purifying, removing, quantifying and/or otherwise generally detecting antibodies that specifically bind to a specified therapeutic protein, e.g., to a VLA-4 binding antibody, or fragments thereof. For example, immunodetection techniques may include, hut are not limited to, enzyme linked immunosorbent assays (ELISA) (including, but not limited to, a standard sandwich ELISA or a bridging ELISA), radioimmunoassays (RIA), immunoradiometric assays, fluoroimmunoassays, chemiluminescent assays, bioluminescent assays, radioimmunoprecipitation assays (RIPA), and Western blots. In addition, immunodetection techniques may include Optical Sensor-based methods, such as surface plasmon resonance (SPR), or guided mode resonance filter (BIND). Although certain examples provided herein relate to assays utilizing an immobilized VLA-4 binding antibody attached to a surface (e.g. an ELISA), one of ordinary skill in the art will recognize that the invention in some aspects may include assays without surface attachment of a VLA-4 binding antibody (e.g. flow cytometric assays, etc.). Other immunodetection techniques may include immunoradiometric assays (IRMA), time-resolved fluorometry (TRF), or electrochemiluminescence (ECL). A number of useful immunodetection methods have been described in the scientific literature, such as, e.g., Doolitle M H and Ben-Zeev 0, 1999; Gulbis B and Galand P, 1993; De Jager R et al., 1993; and Nakamura et al., 1987, each incorporated herein by reference.

In one aspect, an assay is performed to detect a presence of a binding activity for a VLA-4 binding antibody in a biological sample. In one embodiment, the specificity of the binding activity may be evaluated by determining whether the observed binding activity is specific for the VLA-4 binding antibody or whether it is due to an interfering factor that may be present in the biological sample such as a rheumatoid factor or other binding factor.

Aspects of the invention may include an assay that involves contacting a biological sample with an immobilization moiety to immobilize any binding activity that is present in the biological sample. Immobilized binding activity may be detected using a detection moiety. Immobilization and detection moieties may be, respectively, immobilized unlabeled and non-immobilized labeled VLA-4 binding antibodies as described herein. In one embodiment, an immobilization moiety may be bound to a solid substrate or surface (e.g., in a well of a multi-well plate, on the surface of an ELISA plate, etc.). In another embodiment, an immobilization moiety may be attached to a bead (e.g., a magnetic bead) via a covalent or other linkage (e.g., the immobilization moiety may be conjugated to a biotin molecule and attached to a bead coated with streptavidin via a biotin-streptavidin interaction). In some embodiments, the head may be attached to a surface or a matrix. For example, a magnetic bead may be immobilized on a magnetic surface. Similarly, a charged bead may be immobilized on a charged surface (e.g., an electrode).

A positive result may be determined if the detected amount of binding activity (e.g., the amount of binding activity that is captured by the immobilization moiety) is above a predetermined threshold. The specificity of the detected binding activity may be evaluated by including a competition moiety in the assay. The competition moiety may be a non-immobilized unlabeled VLA-4 binding antibody that may be included to compete with the immobilization and/or detection steps of the assay. If the presence of the competition moiety reduces the binding activity by at least a predetermined percentage or cut-off, the binding activity is determined to be specific and the positive result is confirmed. If the presence of the competition moiety fails to reduce the binding activity by at least a predetermined percentage or cut-off, the binding activity is determined to be non-specific and the initial positive result is now determined to be a negative result for an immune response.

According to aspects of the invention, predetermined amounts of immobilization, detection and/or competition moieties may be used. Similarly, an initial threshold level of binding activity may be established using a sample that contains a predetermined amount of an antibody that is known to bind to a VLA-4 binding antibody. For example, a threshold level may be established using between 10 ng and 1,000 ng (e.g., about 50 ng, or about 500 ng) of a control antibody per ml of assay. The amount of antibody used to determine the threshold level will determine the sensitivity of the assay. In general, the sensitivity of the assay may be considered to be similar to the amount of antibody that is used to determine the initial threshold. It should be appreciated that the amount of binding in the control may serve as a reference that is used to determine the threshold (e.g., the threshold amount may be a multiple or a fraction of the signal obtained in the control). However, in one embodiment, the signal obtained in the control assay is used as the threshold amount. It also should be appreciated that the assay sensitivity may be affected by a number of factors including the affinity and specificity of the control antibody.

In one embodiment, the specificity of the binding activity may be evaluated by spiking the assay with an amount of competition moiety that is similar to the amount of control antibody that was used to establish the threshold level of binding. For example, an assay may be spiked with between about 10 ng and 1,000 ng (e.g., about 50 ng, or about 500 ng) of unlabeled soluble VLA-4 binding antibody per ml of assay. However, other amounts of competition moiety may be used.

Accordingly, in some embodiments of the invention, a first level of binding activity, in a biological sample, to the VLA-4 binding antibody is determined in a first immunoassay for a first aliquot of the biological sample, and a second level of binding activity to the VLA-4 binding antibody is determined in a second immunoassay for a second aliquot of the biological sample, wherein the second immunoassay is spiked with a greater amount of unlabeled soluble VLA-4 binding antibody than the first immunoassay, and the presence of at least a threshold level of soluble antibody to the VLA-4 binding antibody is indicated if the first level of binding activity is greater than a reference level and the second level of binding activity is less than a predetermined percentage of the first level of binding activity.

One of ordinary skill in the art will recognize that different methods can be used for assessing and/or monitoring an immune response in a subject who has been treated with a therapeutic antibody such as a VLA-4 binding antibody. For example, as described above, the assessment and/or monitoring may be performed by determining whether the amount of an antibody that specifically binds to a VLA-4 binding antibody using a single-level "cut-off". As used herein the cut-off level of binding is the level at or above which increased detection will be scored as significant and/or positive and a confirmatory determination that the detection of a level of soluble binding activity in a biological sample reflects the level of an antibody that specifically binds to a VLA-4 binding antibody in the sample. In other embodiments, the identification of an immune response to the therapeutic VLA-4 binding antibody may be performed quantitatively to determine a titer of an antibody that specifically binds to a VLA-4 binding antibody in a biological sample from a subject.

In one aspect of the invention, an immunodetection assay may be an ELISA. As will be understood by those of ordinary skill in the art, the term "ELISA" encompasses a number of protocols for immunodetection. For example, ELISA methods include sandwich ELISAs, bridging ELISAs, etc. In some embodiments of the invention, the ELISA immunoassay is a manual assay. However, in some embodiments of the invention all or part of the ELISA may be performed robotically.

In some embodiments of the invention, an ELISA assay includes using a VLA-4 binding antibody as an immobilized target moiety with which an ELISA plate is coated. The coated ELISA plate may then be contacted with a biological sample for determination of the level of a subject antibody that specifically binds a VLA-4 binding antibody. In some embodiments of the invention, a first aliquot of a biological sample is assayed using an ELISA assay to determine the presence or absence of a threshold amount of binding to the immobilized target VLA-4 binding antibody and a second aliquot of the same biological sample is also assayed using an ELISA to confirm whether or not a threshold (or above threshold) level of binding to the immobilized target VLA-4 binding antibody is indicative of a VLA-4 binding antibody-specific antibody. In one aspect of the invention, the threshold level of soluble binding activity in an aliquot is about equal to the level of binding activity present in a control or reference sample comprising at least about 50 ng, 100 ng, 200 ng, 300 ng, 400 ng, 500 ng, 600 ng, 700 ng, 800 ng, 900 ng, or 1,000 ng per ml of a reference antibody that binds to a VLA-4 binding antibody. In one embodiment, the threshold level is determined as about equal to the level of binding activity in a control or reference sample containing about 500 ng/ml of a reference antibody that binds to a VLA-4 binding antibody. The reference antibody may be polyclonal or monoclonal. The reference antibody may be a murine anti-natalizumab antibody (e.g., 12C4 described in Sheremata et al., 1999, Neurology 52, page 1072). As described herein, if the level of binding to the immobilized target VLA-4 binding antibody that is at least at the threshold level, and the soluble binding activity is determined to be the binding activity of an antibody that specifically binds to a VLA-4 binding antibody, then it identifies an immune response to the VLA-4 binding antibody in the subject.

In general, ELISA methods useful in methods of the invention may include obtaining a biological sample from a subject who has been administered a therapeutic antibody such as a VLA-4 binding antibody (e.g. natalizumab, etc.) and contacting an aliquot of the sample with an immobilization antibody. In some embodiments, the immobilization antibody may be the same VLA-4 binding antibody that was administered to the subject. The immobilization antibody captures molecules or compounds in the sample that bind to the antibody, and the sample is contacted with a second detection moiety that is capable of selectively binding to or detecting the molecule or compound that is captured, (e.g., a labeled second antibody). Examples of moieties capable of selectively binding or detecting the complex include, but are not limited to antibodies or other ligands that can be labeled using a variety of markers (e.g., biotin/avidin ligand binding arrangement, as is known in the art). One skilled in the art may also use a labeled third antibody. In preferred embodiments, the second moiety is a labeled form of the immobilization antibody.

In some embodiments of the invention, an ELISA assay includes using the therapeutic VLA-4 binding antibody as an immobilized target moiety with which an ELISA plate is coated. The coated ELISA plate may then be contacted with a biological sample for determination of the level of a subject antibody that specifically binds the therapeutic VLA-4 binding antibody. In some embodiments of the invention, a first aliquot of a biological sample is assayed using an ELISA assay to determine the presence or absence of a threshold amount of binding activity for the immobilized target VLA-4 binding antibody, and a second aliquot of the same biological sample is assayed using an ELISA to confirm whether or not a threshold (or above threshold) level of binding to the immobilized target VLA-4 binding antibody is indicative of a VLA-4 binding antibody-specific antibody. In one aspect of the invention, the threshold level of soluble binding activity in an aliquot is about equal to the level of binding activity present in a control or reference sample comprising at least about 50 ng, 100 ng, 200 ng, 300 ng, 400 ng, 500 ng, 600 ng, 700 ng, 800 ng, 900 ng, or 1,000 ng per ml of a reference antibody that binds to a VLA-4 binding antibody. In one embodiment, the threshold level is determined as about equal to the level of binding activity in a control or reference sample containing about 500 ng/ml a reference antibody that binds to a VLA-4 binding antibody. The reference antibody may be polyclonal or monoclonal. The reference antibody may be a murine anti-natalizumab antibody (e.g., 12C4 described in Sheremata et al., 1999, Neurology 52, page 1072).

A reference antibody that hinds to a VLA-4 binding antibody may be a reference antibody that binds to natalizumab (for example, an antibody that binds to natalizumab with high affinity, e.g., with nanomolar affinity). In some embodiments, a reference antibody that binds to natalizumab may block natalizumab binding to VLA-4 (e.g., it may inhibit binding of natalizumab to VLA-4 by at least 50%, at least 60%, at least 70%, at least 80%, at least 90%, or more). The reference antibody may be a murine monoclonal antibody. In some embodiments, the reference antibody is the 12C4 antibody (available from Maine Biotechnology Services, Inc., Portland Me.; see, e.g., Sheremata et al., 1999, Neurology 52, page 1072). 12C4 is a blocking antibody that blocks natalizumab binding to VLA-4. In some embodiments, the reference antibody competes with 12C4 for binding to natalizumab. Antibody binding competition may be demonstrated using standard methods of assessing an antibody's ability to competitively inhibit the 12C4 antibody's ability to block binding of natalizumab to VLA-4. In some embodiments, the presence of an antibody that specifically binds to a VLA-4 binding antibody is determined using a bridging ELISA. In a bridging ELISA, antibodies that specifically bind to a VLA-4 binding antibody (e.g., from a biological sample) act as a bridge between VLA-4 binding antibody coated on an ELISA plate and detectably labeled VLA-4 binding antibody in solution (e.g., non-immobilized). Thus, an ELISA signal after standard processing indicates that the detectable label has been linked to the solid phase and that a soluble binding activity is present in the biological sample.

Contacting an aliquot of the biological sample with the immobilized antibody under effective conditions and for a period of time sufficient to allow the formation of immune complexes (primary immune complexes) is generally a matter of adding the aliquot of the biological sample to the immobilized antibody (e.g., a VLA-4 binding antibody immobilized on an ELISA plate) and incubating the mixture for a period of time long enough for the immobilized antibody to form an immune complex with (i.e., to bind to) a molecule or compound with soluble binding activity that is present in the aliquot of the biological sample. The molecule or compound with soluble binding activity may be an induced antibody that specifically binds to the VLA-4 binding antibody or may be a non-induced endogenous antibody or receptor that binds to the VLA-4 binding antibody (e.g., a rheumatoid factor [RF] or an anti-Fab antibody). After this time, the sample-antibody mixture (e.g., the ELISA plate, dot blot, or western blot) will generally be washed to remove unbound antibody species and/or materials from the assay mixture.

If a threshold level of binding activity is detected, an additional step may involve confirming whether or not the binding activity is indicative of an induced antibody that specifically binds to the therapeutic VLA-4 binding antibody. For this confirmation step, a second aliquot of the biological sample may be prepared and assayed as described for the first aliquot, except that a predetermined amount of non-immobilized unlabeled competition VLA-4 binding antibody also is added to the assay (e.g., the ELISA assay). For example, the predetermined amount of competition antibody may be an unlabeled amount that reduces a specific signal by about 50% or more in a control assay. If the presence of the unlabeled VLA-4 binding antibody reduces the signal by more than an expected percentage amount, then the threshold (or above threshold) binding activity is judged as a positive indicator for the presence of an antibody that specifically binds to the therapeutic VLA-4 binding antibody. In contrast, if the presence of the unlabeled VLA-4 binding antibody reduces the signal by less than an expected percentage amount then the threshold (or above threshold) binding activity is judged as negative for an antibody that specifically binds to a VLA-4 binding antibody. It should be appreciated that a non-specific signal may be due serum factors other than an antibody that binds to the VLA-4 binding antibody. As used herein the terms "spike" or "spiked" refers to the addition of an unlabeled (or differently labeled) soluble competition VLA-4 binding antibody to a sample or assay.

As used herein, the "percentage reduction" is the percentage of the level of binding determined in the first aliquot. Thus, for example, if there is an indication of about 500 ng/ml equivalent of a molecule or compound with binding activity in the first aliquot and the inclusion of the unlabeled VLA-4 binding antibody in the second aliquot reduces the amount of signal by more than 40-90% (e.g., by about 50% or more, by about 55% or more, by about 60% or more, by about 65% or more, by about 70% or more, by about 75% or more, by about 80% or more, by about 85% or more, by about 90% or more), then the binding activity in the biological sample is considered indicative of the presence of an induced antibody that specifically binds to the therapeutic VLA-4 binding antibody. But if the inclusion of the unlabeled VLA-4 binding antibody in the second aliquot reduces the amount of signal by less than 20-40%, then the binding activity in the biological sample is not considered to be indicative of the presence of an induced antibody that specifically binds to the therapeutic VLA-4 binding antibody. In some embodiments, the competition antibody may be soluble unlabeled natalizumab. In some embodiments, the soluble unlabeled natalizumab may be used at a final concentration of about 100 µg/ml. However, any concentration of free unlabeled natalizumab may be used if it results in a predetermined decrease (e.g., about 40%, about 50%, or more) in the signal obtained for a control sample containing a control amount of reference antibody. For example, a control sample may contain about 500 ng/ml, about 3 µg/ml or any other suitable amount of reference antibody (e.g., 12C4). As indicated herein, the presence in a biological sample from a patient of an antibody that specifically binds to a VLA-4 binding antibody indicates that the subject has a clinically significant immune response to the VLA-4 binding antibody.

In an exemplary "sandwich" ELISA, a therapeutic VLA-4 binding antibody (e.g., natalizumab) may be used as the target antibody and may be immobilized onto a selected surface exhibiting protein affinity, such as a well in a polystyrene microtiter plate. Then, a sample from a subject who has had at least one administration of a therapeutic VLA-4 binding antibody, e.g., natalizumab, is added to the wells. After binding and/or washing to remove non-bound materials, binding molecules or compounds that are bound to the target antibody may be detected. Detection may be achieved by the addition of a second antibody that is linked to a detectable label. In addition, the identity of the binding molecule or compound as an antibody that specifically binds to a VLA-4 binding antibody may be confirmed as described above herein.

As will be understood by those of ordinary skill in the art, notwithstanding individual features (e.g. the confirmatory steps described herein), in general, ELISAs have certain features in common, such as coating, incubating and binding, washing to remove non-specifically bound species, and detecting the bound immune complexes.

In coating a plate with either antigen or antibody, the wells of the plate will generally be incubated with a solution of the target antibody, either overnight or for a specified period of hours. A coating buffer may be a sodium phosphate/BSA coating buffer or another suitable art-known coating buffer. The wells of the plate will then be washed to remove incompletely adsorbed material. Any remaining available surfaces of the wells are then "coated" with a nonspecific protein that is antigenically neutral with regard to the test sample. This protein may be bovine serum albumin (BSA), casein or solutions of milk powder, etc. The coating allows for blocking of nonspecific adsorption sites on the immobilizing surface and thus reduces the background caused by nonspecific binding of anti sera onto the surface.

In an ELISA, a secondary or tertiary detection means may be used or a direct detection means may be used. When using a secondary or tertiary detection methods, after binding of a protein or antibody to the well, coating with a non-reactive material to reduce background, (e.g. with blocking buffer such as Tris-sucrose blocking buffer or other art-recognized blocking buffer), and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand. In preferred embodiments of the invention the second binding ligand is a VLA-4 binding antibody (e.g. the same VLA-4 binding antibody as used for the target antibody).

As used herein, the term "under conditions effective to allow immune complex formation" means that the conditions preferably include diluting the antigens and/or antibodies with solutions such as BSA, bovine gamma globulin (BGG), phosphate buffered saline (PBS)/Tween, PBS with casein and Tween 20, or PBS/BSA buffer with Tween 20. Various other art-known assay diluents can be used in the methods of the invention. These added agents also tend to assist in the reduction of nonspecific background and may include up to 0.5M NaCl.

As used herein, the "suitable" conditions also mean that the incubation is at a temperature or for a period of time sufficient to allow effective binding. Incubation steps are typically from about 1 to 2 to 4 or so, at temperatures preferably on the order of 25° C. to 27° C., or may be overnight at about 4° C. Various art-known assay temperature and timing parameters can be used in the methods of the invention.

After the incubation steps in an ELISA, the contacted surface is washed to remove non-bound material. A preferred washing procedure may include washing with a solution such as PBS/Tween, TBS/Tween, or borate buffer, which may also include up to 0.5M NaCl. Following the formation of specific immune complexes between the test sample and the target antibody, and subsequent washing, the presence of even minute amounts of immune complexes may be determined. It will be understood that additional art-known wash buffer formulations can be used in the methods of the invention.

To provide a detecting means, the second or third antibody will have an associated detectable label. In certain embodiments, the detectable label is an enzyme that will generate color development upon incubating with an appropriate chromogenic substrate. Thus, for example, one may contact or incubate the first and second immune complex with a urease-, glucose oxidase-, alkaline phosphatase-, hydrogen peroxidase-conjugated antibody, or other conjugated antibody for a period of time and under conditions that favor the development of further immune complex formation (e.g., incubation for 2 hours at room temperature in a PBS-containing solution such as PBS-Tween).

It also will be understood by those of skill in the art that one or more positive and negative quality controls may be utilized in the methods of the invention. A positive quality control sample may be a normal serum sample that contains a predetermined amount of an antibody that is known to bind to a VLA-4 binding antibody. Quality control samples may be reacted in parallel with and under the same conditions as the biological and control samples of the assay and provide a measure of the function of the assay. A negative quality control sample may be a serum sample known not to include an antibody that is known to bind to a VLA-4 binding antibody One of ordinary skill will understand how to utilize positive and negative control reactions and samples in an ELISA to ascertain and validate the functionality of the solutions and/or substrates and/or protocol used in the assay. For example, a positive control may include a known amount of an antibody that specifically binds the VLA-4 binding antibody so when treated under the same conditions as the test samples (e.g., the biological sample) it indicates that the assay works within expected parameters. An example of a negative control may be a sample that is known to not include an antibody that specifically binds to the VLA-4 binding antibody. Such a negative control, when treated under the same conditions as the test sample (e.g., the biological sample), will demonstrate that the binding detected in a biological sample arises from the biological sample and is not due to contamination of assay components or other factor not associated with the biological sample. A non-limiting example of an assay encompassed by the methods of the invention may involve the following procedures. Coating the wells of an ELISA plate with a solution of about 0.25 µg/mL natalizumab reference standard in a buffer and incubating the coated plate overnight at ambient temperature; washing the plate wells a least once with a wash buffer and incubating the plate wells with a blocking buffer for a minimum of 1 hour at ambient temperature; diluting control samples and screening samples by about 1:10 in an assay diluent; diluting competition samples and natalizumab (at about 1 mg/mL) together in the assay diluent to a final concentration of natalizumab of about 100 µg/mL and about a 1:10 final dilution of the competition samples; incubating control samples, screening samples, and competition samples about 1 hour at ambient temperature and washing the plate wells at least once with wash buffer; incubating the samples in the plate wells between about 60 and 150 minutes at ambient temperature and washing the plate wells at least three times with wash buffer; adding about 100 µL/plate well of biotinylated-natalizumab diluted to about 1:1000 in the assay diluent, incubating the plate for about 60-90 min at ambient temperature, and washing the plate wells at least three times with wash buffer; adding streptavidin-horseradish peroxidase diluted about 1:5000 in assay diluent to the samples in plate wells, incubating the plate about 60-90 minutes at ambient temperature, and washing the plate at least three times with wash buffer; adding a sufficient amount of color-producing substrate to the plate wells to visualize antibody binding, developing the plate for several minutes at ambient temperature, stopping the development by adding 1N H2SO4 to the plate wells; and reading the plate wells thereby obtaining a result.

It also is contemplated that the ELISA reagents described herein may be packaged in a kit that may be produced commercially to detect the presence of and/or measure an antibody that specifically binds a VLA-4 binding antibody in a biological sample as described herein.

It will also be understood that the controls for use in the invention may include, in addition to predetermined values (such as clinically significant threshold values identified as described herein for a particular therapeutic protein), samples of materials tested in parallel with the experimental materials. Examples include negative control samples (e.g., generated through manufacture) to be tested in parallel with the experimental samples.

As used herein, a biological sample may be, but is not limited to, any of the following: a body fluid of a subject including, blood, serum, plasma, urine, saliva, pleural effusions, stool, synovial fluid, cerebral spinal fluid, mucus, and tissue infiltrations. Preferred body fluids include blood, plasma, and serum. As used herein, biological samples may be obtained using methods well known to those of ordinary skill in the related medical arts. A biological sample may be obtained directly from a subject or may be obtained from cell, tissue, or other culture. A biological sample may be fresh or may have been stored under suitable conditions (e.g., frozen, chilled, etc.) prior to use in methods of the invention.

It should be appreciated that a biological sample may be obtained from a subject at different time intervals after the administration of a therapeutic agent. However, a therapeutic agent may have a characteristic in vivo half-life, and the amount of free therapeutic agent that is present in a biological sample typically will decrease as a function of time after administration of the agent to the subject. The presence of free therapeutic agent (unlabeled and non-immobilized) in a biological sample may interfere with binding and detection reactions of the invention. Accordingly, biological samples should be obtained as long as possible after a therapeutic administration, for example at a "trough" in the treatment cycle. A "trough" represents the lowest amounts of free therapeutic agent that are present in a subject during a treatment cycle. A trough may occur, for example, long after one therapeutic administration and soon before a subsequent therapeutic administration. It should be appreciated that the timing of the trough may be influenced by many factors, including the amount of agent that is administered, the half-life of the agent, the frequency of administration, etc. For example, a monthly administration of a VLA-4 binding antibody (e.g., 300 mg of natalizumab) results in a trough at about 30 days after one administration and immediately before a subsequent administration. However, it should be appreciated that assays of the invention may be performed on samples taken at different times after treatment administration provided that the assays are relatively insensitive to, or account for, the presence of free therapeutic agent in the biological sample. When levels of binding activity are compared for different samples taken at different time points, it may be particularly important to obtain each sample from a similar stage in the treatment cycle (e.g., a similar length of time after a therapeutic administration) so that the results can be interpreted without needing to correct for differences in levels of free therapeutic agent in the biological samples.

It should be appreciated that biological samples may be diluted before being assayed (e.g., 2 fold, 5 fold, 10 fold, 50 fold, 100 fold, and including higher or lower fold values or any fold value in between). In one embodiment, a reference sample containing a clinically significant threshold amount of reference antibody may be diluted by the same amount as the biological sample being tested so that the signal obtained for the biological sample can be compared directly to the signal obtained for the reference sample.

In some embodiments of the invention, one or more aliquots from a biological sample are used. As used herein, the term "aliquot" means a portion or part of the biological sample. In some embodiments, two or more aliquots may be taken from a biological sample obtained from a subject and the aliquots can be tested using methods of the invention to determine the presence of an immune response to a VLA-4 binding antibody in the subject. For example, two substantially equivalent aliquots can be taken from a biological sample obtained from a subject to whom a VLA-4 binding antibody (e.g. natalizumab) has been administered, and a level of soluble binding activity can be detected in one aliquot (e.g. a "first" aliquot) can be determined. Additionally, the other aliquot (e.g. the "second" aliquot) may be assessed using the methods of the invention to determine whether the soluble binding activity detected in the first aliquot, which would also be present in the second aliquot by virtue of their common sample origin, is an antibody that specifically binds a VLA-4 binding antibody. In some embodiments, if at least a threshold level of binding is present in the first aliquot and the soluble binding activity is determined to be the activity of an antibody that specifically binds a VLA-4 binding antibody, it identifies that an immune response to the VLA-4 binding antibody is present in the subject.

VLA-4 Binding Antibodies

Aspects of the invention relate to detection assay(s) for identifying and/or monitoring an immune response to one or more therapeutic VLA-4 binding antibodies that are administered to a subject. In certain aspects of the invention, a detection assay involves both immobilization and detection moieties. In some embodiments, a detection assay also may include a competition moiety. As described herein, an immobilization moiety may be used to immobilize an induced antibody (e.g., a serum antibody) that hinds to the VLA-4 binding antibody. A detection moiety may be used to detect the immobilized antibody. A competition moiety may be used to compete with the either the immobilization and/or detection moiety for binding to the induced antibody in order to determine the specificity of binding to the induced antibody. The immobilization and detection moieties may bind independently to one or more antibodies that are characteristic of an immune response to a VLA-4 binding antibody. Accordingly, the immobilization and detection moieties may be the same VLA-4 binding antibody that was administered to the subject (e.g., the immobilization moiety may be an immobilized form of the therapeutic VLA-4 binding antibody that was administered to the subject, and the detection moiety may be a labeled form of the therapeutic VLA-4 binding antibody that was administered to the subject). However, in other embodiments, each of the immobilization and detection moieties independently may be variants of the therapeutic VLA-4 binding antibody that was administered to the subject, provided that the immobilization and detection moieties bind with suitable affinity to detect one or more induced antibodies (e.g., serum antibodies) against the therapeutic VLA-4 binding antibody. The competition moiety is typically a soluble unlabeled (or differentially labeled) form of the immobilization or detection moiety. However, the competition moiety may be a variant of the immobilization or detection moiety, provided that it competes sufficiently for binding to the therapeutic VLA-4 binding antibody to determine the specificity of the binding activity detected in the assay.

According to aspects of the invention, any one or more VLA-4 binding antibodies (including natalizumab and/or related VLA-4 binding antibodies) may be used therapeutically. Accordingly, any one or more of the VLA-4 binding antibodies may be used as immobilization, detection, and/or competition moieties in a detection assay of the invention. In one embodiment, a VLA-4 binding antibody may be an IgG antibody (e.g., an IgG4 antibody). In another embodiment, a VLA-4 binding antibody may be polyclonal or monoclonal. In yet another embodiment, a VLA-4 binding antibody may be a humanized version of a murine antibody.

Natalizumab and related VLA-4 binding antibodies are described, e.g., in U.S. Pat. No. 5,840,299. mAb 21.6 and HP1/2 are exemplary murine monoclonal antibodies that bind VLA-4. Natalizumab is a humanized version of murine mAb 21.6 (see, e.g., U.S. Pat. No. 5,840,299). A humanized version of HP1/2 has also been described (see, e.g., U.S. Pat. No. 6,602,503). Several additional VLA-4 binding monoclonal antibodies, such as HP2/1, HP2/4, L25 and P4C2, are described (e.g., in U.S. Pat. No. 6,602,503; Sanchez-Madrid et al., 1986 Eur. J. Immunol., 16:1343-1349; Hemler et al., 1987 J. Biol. Chem. 2:11478-11485; Issekutz and Wykretowicz, 1991, J. Immunol., 147: 109 (TA-2 mab); Pulido et al., 1991 J. Biol. Chem., 266(16):10241-10245; and U.S. Pat. No. 5,888,507). Many useful VLA-4 binding antibodies interact with VLA-4 on cells, e.g., lymphocytes, but do not cause cell aggregation. However, other anti-VLA-4 binding antibodies have been observed to cause such aggregation. HP1/2 does not cause cell aggregation. The HP1/2 MAb (Sanchez-Madrid et al., 1986 Eur. J. Immunol., 16:1343-1349) has an extremely high potency, blocks VLA-4 interaction with both VCAM1 and fibronectin, and has the specificity for epitope B on VLA-4. This antibody and other B epitope-specific antibodies (such as B1 or B2 epitope binding antibodies; Pulido et al., 1991 J. Biol. Chem., 266(16):10241-10245) represent one class of useful VLA-4 binding antibodies.

An exemplary VLA-4 binding antibody has one or more CDRs, e.g., all three HC CDRs and/or all three LC CDRs of a particular antibody disclosed herein, or CDRs that are, in sum, at least 80, 85, 90, 92, 94, 95, 96, 97, 98, or 99% identical to such an antibody, e.g., natalizumab. In one embodiment, the H1 and H2 hypervariable loops have the same canonical structure as those of an antibody described herein. In one embodiment, the L1 and L2 hypervariable loops have the same canonical structure as those of an antibody described herein.

In one embodiment, the amino acid sequence of the HC and/or LC variable domain sequence is at least 70, 80, 85, 90, 92, 95, 97, 98, 99, or 100% identical to the amino acid sequence of the HC and/or LC variable domain of an antibody described herein, e.g., natalizumab. The amino acid sequence of the HC and/or LC variable domain sequence can differ by at least one amino acid, but no more than ten, eight, six, five, four, three, or two amino acids from the corresponding sequence of an antibody described herein, e.g., natalizumab. For example, the differences may be primarily or entirely in the framework regions.

The amino acid sequences of the HC and LC variable domain sequences can be encoded by a sequence that hybridizes under high stringency conditions to a nucleic acid sequence described herein or one that encodes a variable domain or to a nucleic acid encoding an amino acid sequence described herein. In one embodiment, the amino acid sequences of one or more framework regions (e.g., FR1, FR2, FR3, and/or FR4) of the HC and/or LC variable domain are at least 70, 80, 85, 90, 92, 95, 97, 98, 99, or 100% identical to corresponding framework regions of the HC and LC variable domains of an antibody described herein. In one embodiment, one or more heavy or light chain framework regions (e.g., HC FR1, FR2, and FR3) are at least 70, 80, 85, 90, 95, 96, 97, 98, or 100% identical to the sequence of corresponding framework regions from a human germline antibody.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

The skilled artisan will realize that conservative amino acid substitutions may be made in VLA-4 binding antibodies to provide functionally equivalent variants, of the antibodies, i.e, the variants retain the functional capabilities of the VLA-4 polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Exemplary functionally equivalent variants of VLA-4 binding antibodies include conservative amino acid substitutions of in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

As used herein, the term "hybridizes under high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. High stringency hybridization conditions include hybridization in 6×SSC at about 45° C., followed by one or more washes in 0.2×SSC, 0.1% SDS at 65° C., or substantially similar conditions.

Antibodies can be tested for a functional property, e.g., VLA-4 binding, e.g., as described in U.S. Pat. No. 6,602,503.

Antibody Generation

Antibodies that bind to VLA-4 can be generated by immunization, e.g., using an animal. All or part of VLA-4 can be used as an immunogen. For example, the extracellular region of the alpha-4 subunit can be used as immunogen. In one embodiment, the immunized animal contains immunoglobulin producing cells with natural, human, or partially human immunoglobulin loci. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XenoMouse™, Green et al. Nature Genetics 7:13-21 (1994), US Published Patent Application No. 2003-0070185, U.S. Pat. No. 5,789,650, and WO 96/34096. Non-human antibodies to VLA-4 can also be produced, e.g., in a rodent. The non-human antibody can be humanized, e.g., as described in U.S. Pat. No. 6,602,503, EP 239 400, U.S. Pat. Nos. 5,693,761, and 6,407,213.

EP 239 400 (Winter et al.) describes altering antibodies by substitution (within a given variable region) of their complementarity determining regions (CDRs) for one species with those from another. CDR-substituted antibodies are predicted to be less likely to elicit an immune response in humans compared to true chimeric antibodies because the CDR-substituted antibodies contain considerably less non-human components. (Riechmann et al., 1988, Nature 332, 323-327; Verhoeyen et al., 1988, Science 239, 1534-1536). Typically, CDRs of a murine antibody substituted into the corresponding regions in a human antibody by using recombinant nucleic acid technology to produce sequences encoding the desired substituted antibody. Human constant region gene segments of the desired isotype (usually gamma I for CH and kappa for CL) can be added and the humanized heavy and light chain genes are co-expressed in mammalian cells to produce soluble humanized antibody.

Queen et al., 1989 Proc Natl Acad Sci USA. December; 86(24):10029-33 and WO 90/07861 have described a process that includes choosing human V framework regions by computer analysis for optimal protein sequence homology to the V region framework of the original murine antibody, and modeling the tertiary structure of the murine V region to visualize framework amino acid residues which are likely to interact with the murine CDRs. These murine amino acid residues are then superimposed on the homologous human framework. See also U.S. Pat. Nos. 5,693,762; 5,693,761; 5,585,089; and 5,530,101. Tempest et al., 1991, Biotechnology 9, 266-271) utilize, as standard, the V region frameworks derived from NEWM and REI heavy and light chains respectively for CDR-grafting without radical introduction of mouse residues. An advantage of using the Tempest et al., approach to construct NEWM and REI based humanized antibodies is that the three-dimensional structures of NEWM and REI variable regions are known from x-ray crystallography and thus specific interactions between CDRs and V region framework residues can be modeled.

Non-human antibodies can be modified to include substitutions that insert human immunoglobulin sequences, e.g., consensus human amino acid residues at particular positions, e.g., at one or more of the following positions (preferably at least five, ten, twelve, or all): (in the FR of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the FR of the variable domain of the heavy chain) 2H, 4H, 24H, 36H, 37H, 39H, 43H, 45H, 49H, 58H, 60H, 67H, 68H, 69H, 70H, 73H, 74H, 75H, 78H, 91H, 92H, 93H, and/or 103H (according to the Kabat numbering). See, e.g., U.S. Pat. No. 6,407,213.

As will be apparent to one of ordinary skill in the art, the present invention also provides for F(ab')2, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences.

In certain embodiments, a VLA-4 binding antibody may be a VLA-4 single-chain antibody, a single-domain antibody, or a Nanobody™. Characteristics of each of these antibody types and methods for their use are well known in the art. Nanobodies™ are the smallest functional fragments of antibodies and are derived from naturally occurring single-chain antibodies (see Ablynx, Belgium; ablynx.com). Nanobody™ technology was developed following the discovery that camelidae (camels and llamas) possess a unique repertoire of fully functional antibodies that lack light chains. Nanobody™ structure consists of a single variable domain (VHH), a hinge region, and two constant domains (CH2 and CH3). The cloned and isolated VHH domain is a stable polypeptide harboring the full antigen-binding capacity of the original heavy chain. Nanobodies™ combine the features of conventional antibodies with features of small molecule drugs. Nanobodies™ show high target specificity and low inherent toxicity. Additionally, Nanobodies™ are very stable, can be administered by means other than injection, and are easy to manufacture. In certain embodiments, a therapeutic VLA-4 binding antibody, an immobilization moiety, and/or a detection moiety may be a humanized Nanobody™.

Antibody Production

Fully human monoclonal antibodies that bind to VLA-4 can be produced, e.g., using in vitro-primed human splenocytes, as described by Boerner et al., 1991, J. Immunol., 147, 86-95. They may be prepared by repertoire cloning as described by Persson et al., 1991, Proc. Nat. Acad. Sci. USA, 88: 2432-2436 or by Huang and Stollar, 1991, J. Immunol. Methods 141, 227-236. U.S. Pat. No. 5,798,230. Large nonimmunized human phage display libraries may also be used to isolate high affinity antibodies that can be developed as human therapeutics using standard phage technology (see, e.g., Vaughan et al, 1996 Nat Biotechnol. March; 14(3):309-14; Hoogenboom et al. (1998) Immunotechnology 4:1-20; and Hoogenboom et al. (2000) Immunol Today 2:371-8; US Published Patent Application No. 2003-0232333). Antibodies can be produced in prokaryotic and eukaryotic cells. In one embodiment, the antibodies (e.g., scFvs) are expressed in a yeast cell such as Pichia (see, e.g., Powers et al. (2001) J Immunol Methods. 251:123-35), Hanseula, or Saccharomyces. In one embodiment, antibodies, particularly full length antibodies, e.g., IgGs, are produced in mammalian cells. Exemplary mammalian host cells for recombinant expression include Chinese Hamster Ovary (CHO cells) (including dhfr-CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159: 601-621), lymphocytic cell lines, e.g., NS0 myeloma cells and SP2 cells, COS cells, K562, and a cell from a transgenic animal, e.g., a transgenic mammal. For example, the cell is a mammary epithelial cell.

In addition to the nucleic acid sequence encoding the immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). Exemplary selectable marker genes include the dihydrofolate reductase (DHFR) gene (for use in dhfr-host cells with methotrexate selection/amplification) and the neo gene (for G418 selection).

In an exemplary system for recombinant expression of an antibody (e.g., a full length antibody or an antigen-binding portion thereof), a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. For example, some antibodies can be isolated by affinity chromatography with a Protein A or Protein G. U.S. Pat. No. 6,602,503 also describes exemplary methods for expressing and purifying a VLA-4 binding antibody.

Antibodies may also include modifications, e.g., modifications that alter Fc function, e.g., to decrease or remove interaction with an Fc receptor or with C1q, or both. For example, the human IgG1 constant region can be mutated at one or more residues, e.g., one or more of residues 234 and 237, e.g., according to the numbering in U.S. Pat. No. 5,648,260. Other exemplary modifications include those described in U.S. Pat. No. 5,648,260.

For some antibodies that include an Fc domain, the antibody production system may be designed to synthesize antibodies in which the Fc region is glycosylated. For example, the Fc domain of IgG molecules is glycosylated at asparagine 297 in the CH2 domain. This asparagine is the site for modification with biantennary-type oligosaccharides. This glycosylation participates in effector functions mediated by Fcy receptors and complement C1q (Burton and Woof (1992) Adv. Immunol. 51:1-84; Jefferis et al. (1998) Immunol. Rev. 163:59-76). The Fc domain can be produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method for expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

As used herein, the VLA-4 binding antibodies of the invention may be substantially full length VLA-4 binding antibodies or functional fragments thereof. For example, if a fragment of a VLA-4 binding antibody is sufficient to allow specific binding by an antibody that specifically binds a VLA-4 binding antibody it is a functional VLA-4 binding antibody and may be used in the methods and kits of the invention. One of ordinary skill in the art will be able to identify VLA-4 binding antibody fragments and determine whether a VLA-4 binding antibody fragment is a functional VLA-4 binding antibody fragment using only routine procedures and binding assays. Thus, descriptions and examples of methods of using immobilized and non-immobilized VLA-4 binding antibodies that are provided herein, also apply to the use of functional immobilized and non-immobilized VLA-4 binding antibody fragments.

Labels and Detection

Aspects of the invention include using non-immobilized, anti-therapeutic protein antibodies (e.g., VLA-4 binding antibodies) as detection moieties to assess the presence and/or level of soluble binding activity that is bound to an immobilized antibody against a therapeutic protein (e.g., a target VLA-4 binding antibody). Methods to evaluate the presence and/or level of soluble binding activity may include the use of one or more labeled detection moieties (e.g., a VLA-4 binding antibody containing or attached to a detectable label). A detectable label is defined as any moiety that can be detected using an assay. The antibodies and functional antibody fragments of the invention can be coupled to specific labeling agents for detecting binding according to standard coupling procedures. A wide variety of detectable labels can be used, such as those that provide direct detection (e.g., a radioactive label, a fluorophore, [e.g. Green Fluorescent Protein (GFP), Red Fluorescent Protein (RFP), etc.], a chromophore, an optical or electron dense label, etc.) or indirect detection (e.g., an enzyme tag such as horseradish peroxidase, etc.). Non-limiting examples of detectable labels that have been attached to or incorporated into antibodies include: enzymes, radiolabels, fluorescent labels, phosphorescent molecules, chemiluminescent molecules, chromophores, luminescent molecules, photoaffinity molecules, and colored particles or ligands such as biotin, etc. In addition, detection methods of the invention may include electrochemiluminescence methods (ECL).

A variety of methods may be used to detect a label, depending on the nature of the label and other assay components. Labels may be directly detected through optical or electron density, radioactive emissions, non-radiative energy transfers, etc. or indirectly detected with antibody conjugates, streptavidin-biotin conjugates, etc. Many additional detectable labels are known in the art, as are methods for their attachment to antibodies.

Labeled antibodies of the invention may be antibodies that are used in vitro, e.g., in an immunoassay such as an ELISA. Such detectably labeled antibodies may be antibodies that have a detectable label incorporated into the antibody or may be antibodies that are linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Numerous methods for the attachment or conjugation of an antibody to its detectable label are known in the art. An attachment method may include the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3 .alpha.-6 .alpha.-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Antibodies may be labeled with fluorescein markers in the presence of these coupling agents or by reaction with an isothiocyanate. In other embodiments, antibodies may be labeled by derivatization, for example, by selectively introducing sulfhydryl groups in the Fc region of the antibody, using reaction conditions that do not alter the antibody recognition site.

The detection of the detectable label in an assay of the invention is also referred to herein as detecting the "signal". Methods for detecting the signal in an immunoassay are well known in the art. In some important embodiments of the invention, the assay signal can be detected using with a multi-well plate reader (e.g. microplate reader) to assess the amount and/or location of a signal. Signal detection can be optical detection or other detection means suitable for detecting a detectable label utilized in the invention. Additional methods for detecting labels are well known in the art and can be used in methods of the invention. Methods of the invention include ELISAs that have a sensitivity for detecting an antibody that specifically binds to a VLA-4 binding antibody, wherein the sensitivity is at least about 1000 ng, 500 ng, or 50 ng. In preferred embodiments, the ELISA sensitivity for detecting an antibody that specifically binds to a VLA-4 binding antibody is at least about 500 ng.

In general, the detection of immunocomplex formation may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

It should be appreciated that techniques described herein to obtain and produce a VLA-4 binding antibody (e.g., natalizumab) also may be used to obtain and produce a reference antibody that hinds to the VLA-4 binding antibody with high affinity (for example, a high affinity natalizumab binding antibody (e.g., 12C4).

Kits

The invention also relates, in part, to kits for assaying the presence of an immune response to a VLA-4 binding antibody in a sample. An example of such a kit may include the above-mentioned antibodies including, but not limited to Natalizumab or other VLA-4 binding antibody, or a fragment thereof. A kit may include detectably labeled and/or unlabeled antibodies and may include solutions and compounds for detectably labeling an antibody. A kit of the invention may also include one or more of the following components: plates, pipettes, vials, detectable label, solutions (e.g. blocking buffer, wash buffer, binding solutions, diluent solutions, etc), positive and/or negative control samples and solutions. A kit of the invention may also include written instructions for the use of the kit for the identification of an immune response to a VLA-4 binding antibody in a biological sample. Kits of the invention may also include additional components useful in the performance of positive and/or negative ELISA control assays. A kit of the invention may also include equipment such as plate readers and/or robotic instrumentation for use in the methods of the invention.

EXAMPLES

Example 1: Natalizumab Immunogenicity Assay

The assay format and design was based upon a bridging enzyme-linked Immunosorbent assay (ELISA). Standard reagents and procedures suitable for bridging assays were used. In brief, using standard procedures natalizumab was adsorbed to the surface of microtiter plates followed by a blocking step to minimize non-specific binding of serum antibodies. Controls and samples were diluted and added to the wells. Using standard procedures, detection of bound anti-natalizumab antibodies was accomplished by incubating the plates with biotin-natalizumab followed by streptavidin-Alkaline Phosphatase (SA-AP). The color development was proportional to the amount of anti-natalizumab antibody bound.

Natalizumab was diluted to a specific concentration in plate coating buffer was incubated in 96-well microtiter ELISA plates overnight at ambient temperatures. The recommended volume was 100 µl/well. The plates were washed with washing buffer then incubated with blocking buffer at ambient temperatures for >1 hr. The volume of blocking buffer was 200 µl/well. The plates were washed with washing buffer and then incubated with quality control and subject (patient) samples diluted 1:10 in assay diluent with or without added natizumab (100 µg/ml final concentration) at ambient temperatures for 2 hr±15 min. The assay diluent containing added natalizumab represented a confirmatory step. The volume for the assay diluent was 100 µl/well. The plates were then washed in washing buffer, and then incubated with SA-AP at ambient temperatures for 30-35 min. The volume for the incubation with SA-AP was 100 µl/well. The plates were then washed in washing buffer, and then incubated with AP substrate, p-nitrophenyl phosphate (PNPP) at ambient temperatures for 45-50 min. The volume for the incubation in the AP substrate was 100 µl/well. Stop solution (e.g. H2SO4, etc.) was then added directly to the substrate reaction mixture and the optical density (OC) was read at 405 nm.

For assay acceptance the positive and negative controls had to provide results within a pre-defined value and precision. For the assessment of subject (patient) samples results, the samples were judged as negative if their OD value fell below the defined negative cut-off quality control sample. Samples were also judged negative if their OD value fell above the defined negative cut-off quality control sample and the inhibition of the subject (patient) sample signal by added natalizumab in the confirmatory step was less than a pre-defined percent. Samples were judged positive if their OD value fell above the defined negative cut-off quality control sample and the inhibition of the subject (patient) sample signal by added natalizumab in the confirmatory step was greater than or equal to a pre-defined percent.

Example 2: Screening Assay for an Immune Response to a VLA-4 Antibody

A screening assay (as described above) was performed on samples from subjects who had been administered natalizumab. The presence of an immune response to a VLA-4 antibody was examined in patients who had undergone natalizumab administration.

Biological samples from subjects who had been administered natalizumab were tested for the presence of a soluble antibody that specifically binds natalizumab using the methods described in Example 1.

The tests included the use of a high affinity mAb as a positive control. The high affinity mAb detected binding antibodies (e.g. antibodies that bound natalizumab) that were present in biological samples from subjects. The negative cut-off level was determined to the lowest concentration that returned acceptable accuracy/precision (25%/25%); 50 ng/mL in 10% serum. The sensitivity of the mAb was 500 ng/mL in neat (undiluted) serum. With respect to sensitivity, the mAb was determined to detect anti-natalizumab Abs but to be insensitive to irrelevant human monoclonal antibodies. The interference with the mAb by other molecules or components of the samples was determined to include interference by free drug at an mAb:drug ratio of greater than 1:2. FIG. 1 illustrates the effects of free natalizumab interference with the immunoassay for anti-natalizumab antibodies. Rheumatoid factor was also found to interfere with the assay.

Figure 2:
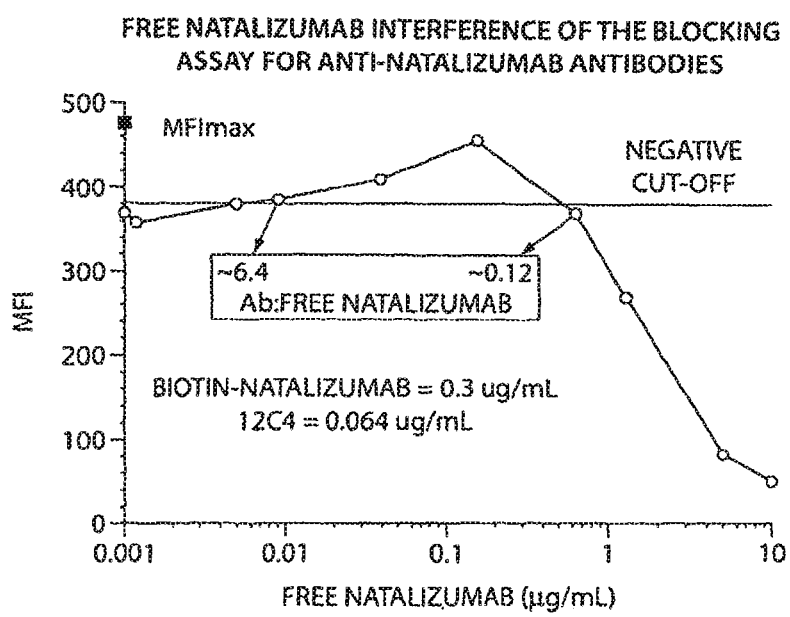
FIG. 2 illustrates the interference of free natalizumab in a blocking assay.

In addition to the screening assay described in Examples 1 and 2, characterization assays to assess binding in the screening assays were also preformed. Biological samples from subjects who had been administered natalizumab were tested for the presence of a soluble antibody that specifically binds natalizumab using a flow cytometry blocking assay. A high affinity mAb was used as a positive control. The assay detected blocking antibodies. The negative cut-off level for the mAb used was determined at 3-4 standard deviations above the mean of measured levels in sera obtained from non-dosed patients. There was a 5% false-positive rate and the sensitivity of the assay was 500 ng/ml of neat serum. The specificity of the mAb was tested and the mAb was determined to detect anti-natalizumab antibodies but was found to be insensitive to irrelevant human monoclonal antibodies. Free-drug interference with the assay was also examined. The assay showed the presence of free-drug interference. Results from an assessment of blocking assay interference by free drug are shown in FIG. 2.

Blocking Assay for Natalizumab

Results

The positive results of the screening and blocking assays were compared. There were 217 Blocking assay positives and 222 Screening assay positives, thus there was a difference of 5% and a percent concordance of 98%. Accordingly, the screening assay provides an accurate measure of a subject's immune response to a therapeutic VLA-4 binding antibody.

Example 3

A screening assay (as described in Examples 1 and 2) was performed on samples from 625 subjects who had been administered natalizumab. The presence of an immune response to a VLA-4 antibody was examined in patients who had undergone natalizumab administration. Incidence of antibodies to natalizumab in the patients examined was: 91% (569 patients) antibody negative and 9% (56 patients) "binding antibody" positive at any time point with 3% (19 patients) "transiently" positive and 6% (37 patients) "persistently" positive. The transient positive patients had detectable antibodies (at a concentration of >0.5 µg/ml) at a single time point, but negative for antibodies at all other time points. The persistent positive patients had detectable antibodies at two or more time points that were at least 42 days apart, or at a single time point with no follow-up samples tested.

Figure 3:
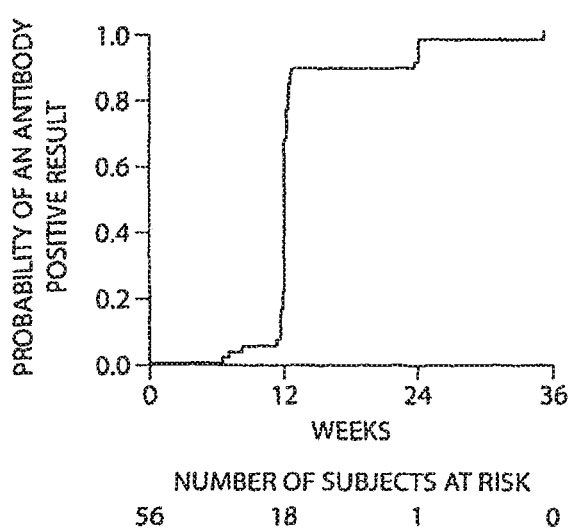
FIG. 3 shows a probability of a clinically significant immune response as a function of time after an initial administration of natalizumab.

FIG. 3 shows the time of first positive results in patients who developed any antibodies. Six percent of patients developed "persistent" antibodies to natalizumab. Over 90% of persistent-positive patients first had detectable antibodies at week 12. No subject became positive for persistent antibodies after week 36. Transient-positive patients had detectable antibodies at week 12, but were subsequently antibody negative.

Figure 4:
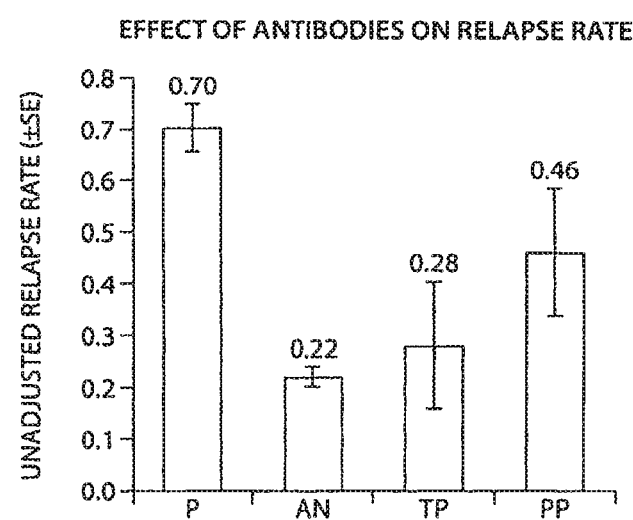
FIG. 4 illustrates an overall effect of positive immune responses on relapse rates. P=Placebo, n=315. AN=Antibody Negative, n=569. TP=Transient Positive, n=19. PP=Persistent Positive, n=37.
Figure 5A:
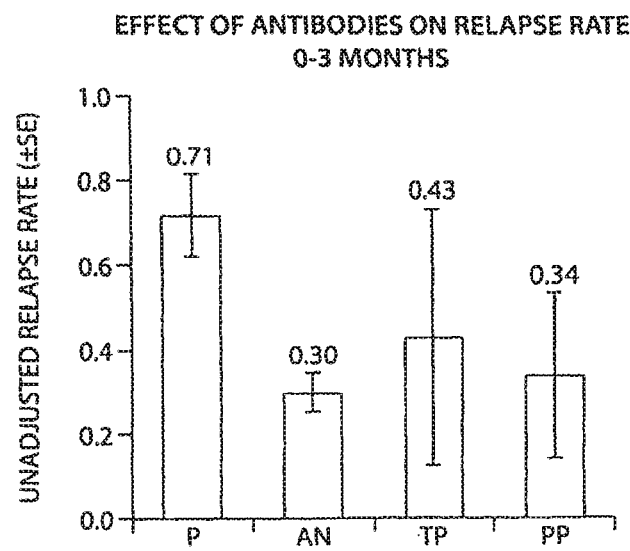
FIGS. 5A-5D illustrate the effect of positive immune responses on relapse rates over particular time intervals after an initial administration of natalizumab (FIG. 5A: 0-3 months, FIG. 5B: 3-6 months, FIG. 5C: 6-9 months, and FIG. 5D: 9-12 months). P=Placebo, n=315. AN=Antibody Negative, n=569. TP=Transient Positive, n=19. PP=Persistent Positive, n=37.
Figure 5B:
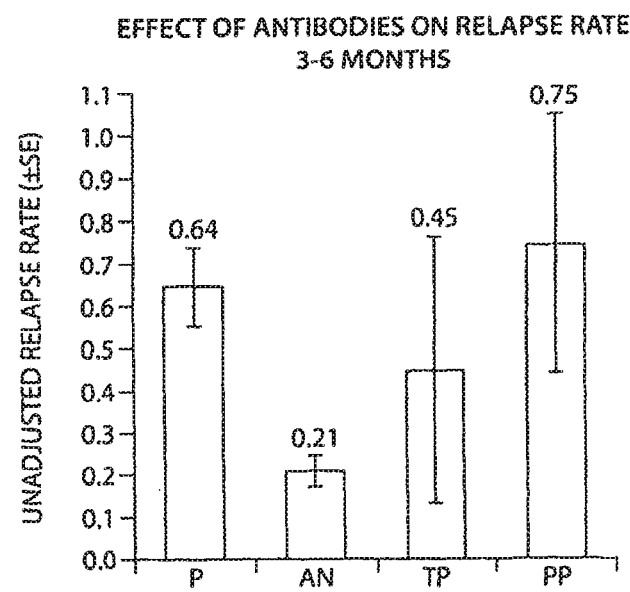
Figure 5C:
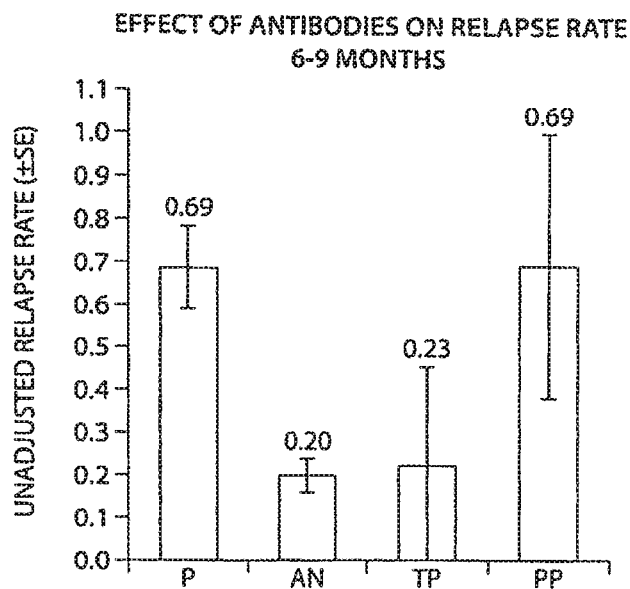
Figure 5D:
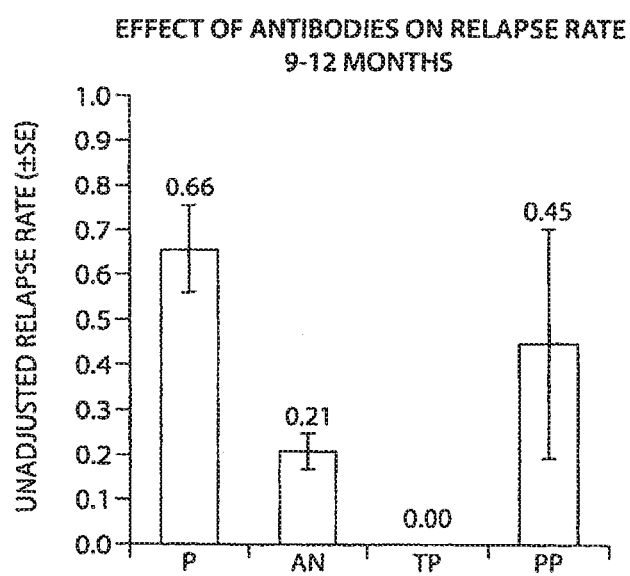

The results were analyzed to determine the presence of an effect of antibodies on the rate of relapse of the original disorder in the patients treated. FIG. 4 illustrates the overall effect of antibodies on relapse rate. The relapse rate was also assessed for subjects with respect to the time elapsed from the administration of the natalizumab. FIG. 5A-D depict the rate of relapse at 0-3 months, 3-6 months, 6-9 months, and 9-12 months respectively.

Results

The results indicated that there is no apparent effect of antibodies during the first three months of treatment. From three to six months the "transient" antibody-positive patients showed diminution in efficacy of the natalizumab treatment. "Persistent" antibody-positive patients showed lost of efficiency of natalizumab treatment. From six to twelve months, full efficacy was restored in "transient" antibody-positive patients, but not in "persistent" antibody-positive patients. Accordingly it is important to identify transient antibody-positive patients as a target population for continued VLA-4 binding antibody therapy.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method of adjusting a natalizumab therapeutic regimen in a patient who has been administered natalizumab, the method comprising detecting a level of serum antibody to natalizumab from two or more biological samples taken at different time points from the patient, and discontinuing the natalizumab therapeutic regimen when the level of serum antibody to natalizumab is above a predetermined clinically relevant threshold, wherein said clinically relevant threshold is equal to about 500 ng/mL.

2. The method of claim 1, wherein the level of serum antibody to natalizumab is measured in a first aliquot of each of the two or more biological samples; and wherein the method further comprises determining the binding specificity of the serum antibody to natalizumab.

3. The method of claim 2, wherein the binding specificity of the serum antibody to natalizumab is determined in a second aliquot of each of the two or more biological samples.

4. The method of claim 1, wherein the level of serum antibody to natalizumab is determined by comparing levels of binding to a labeled natalizumab measured in the presence of two or more different amounts of unlabeled natalizumab.

5. The method of claim 1, wherein the level of serum antibody to natalizumab is determined by comparing levels of binding to an immobilized natalizumab measured in the presence of two or more different amounts of soluble natalizumab.

6. The method of claim 4, wherein the level of serum antibody to natalizumab is determined by comparing a first level of binding to a labeled natalizumab measured in the presence of a first amount of unlabeled natalizumab to a second level of binding to a labeled natalizumab measured in the presence of a second amount of unlabeled natalizumab.

7. The method of claim 1, wherein a bridging ELISA assay is performed to determine whether the two or more biological samples contain the threshold level of antibody to natalizumab.

8. The method of claim 1, wherein a first level of binding to natalizumab is determined in a first immunoassay for a first aliquot of each of the two or more biological samples, and wherein a second level of binding to natalizumab is determined in a second immunoassay for a second aliquot of each of the two or more biological samples, wherein the second immunoassay is spiked with a greater amount of unlabeled soluble natalizumab than the first immunoassay, and wherein the biological sample contains at least a threshold level of serum antibody to natalizumab if the first level of binding is greater than a reference level and the second level of binding is less than the first level of binding.

9. The method of claim 8, wherein the reference level is a level of binding measured for a reference amount of antibody that binds to natalizumab.

10. The method of claim 8, wherein the first and second immunoassays are bridging ELISA assays.

11. The method of claim 1, wherein said patient has multiple sclerosis.

* * * * *